(12) United States Patent
Griffith et al.

(10) Patent No.: US 7,837,466 B2
(45) Date of Patent: Nov. 23, 2010

(54) ORTHODONTIC APPARATUS AND METHOD

(76) Inventors: Richard J. Griffith, 8650 Hunting Hills Dr., Kirtland Hills, OH (US) 44094; William Koenig, 7458 Shadowbrook Dr., Kirtland, OH (US) 44094

( * ) Notice: Subject to any disclaimer, the term of this patent is extended or adjusted under 35 U.S.C. 154(b) by 176 days.

(21) Appl. No.: 11/697,729

(22) Filed: Apr. 8, 2007

(65) Prior Publication Data

US 2008/0248439 A1 Oct. 9, 2008

(51) Int. Cl.
*A61C 3/00* (2006.01)
(52) U.S. Cl. .......................... 433/17; 433/10
(58) Field of Classification Search ............. 433/8–12, 433/5, 11, 17, 20, 22, 17–1, 228
See application file for complete search history.

(56) References Cited

U.S. PATENT DOCUMENTS

| | | | | |
|---|---|---|---|---|
| 1,280,628 | A | * 10/1918 | Angle | 433/14 |
| 3,052,028 | A | * 9/1962 | Wallshein | 433/11 |
| 3,464,113 | A | * 9/1969 | Silverman et al. | 433/11 |
| 3,903,604 | A | * 9/1975 | Snead | 433/5 |
| 4,892,479 | A | * 1/1990 | McKenna | 433/20 |
| 4,897,035 | A | * 1/1990 | Green | 433/17 |
| 4,936,774 | A | * 6/1990 | Stoller et al. | 433/110 |
| 4,958,414 | A | 9/1990 | Benoit | |
| 5,328,235 | A | 7/1994 | Saul et al. | |
| 5,857,850 | A | 1/1999 | Voudouris | |
| 5,908,293 | A | 6/1999 | Voudouris | |
| 5,913,680 | A | 6/1999 | Voudouris | |
| 6,071,118 | A | 6/2000 | Damon | |
| 6,142,775 | A | 11/2000 | Hansen et al. | |

(Continued)

FOREIGN PATENT DOCUMENTS

EP 0583095 * 2/1994

(Continued)

OTHER PUBLICATIONS

Koji Noda, A New Idea and Method of Tooth Movement Using a Rachet Bracket, European Journal of Orthodontics, 29, 2007, 225-231, Published Oxford University Press on Behalf of European Orthdontic Society.

(Continued)

*Primary Examiner*—Cris L Rodriguez
*Assistant Examiner*—Yogesh Patel
(74) *Attorney, Agent, or Firm*—Woodling, Krost and Rust

(57) ABSTRACT

An orthodontic device includes a bracket having a body and the body includes external surfaces. An archwire passageway is formed in the body. An aperture extends from one of the external surfaces of the body to the passageway. A pawl is attached to the body and includes stop and cam surfaces which extend into the aperture. An extendable archwire includes an adjustment portion having a locking surface and a loop-spring therein and the adjustment portion is inserted into and through the passageway. The pawl and the locking surface form a ratchet. The cam surface of the pawl interengages the extendable archwire as the extendable archwire is extended through the bracket under the application of force to the extendable archwire. The stop surface of the pawl interengages the locking surface of the adjustment portion of the extendable archwire preventing retraction of the extendable archwire upon discontinuation of the application of force.

10 Claims, 27 Drawing Sheets

U.S. PATENT DOCUMENTS

| | | | |
|---|---|---|---|
| 6,183,250 B1 * | 2/2001 | Kanno et al. | 433/17 |
| 6,193,508 B1 | 2/2001 | Georgakis | |
| 6,257,883 B1 | 7/2001 | Voudouris | |
| 6,257,884 B1 * | 7/2001 | Chang | 433/18 |
| 6,283,996 B1 * | 9/2001 | Chervitz et al. | 623/13.14 |
| 6,302,688 B1 | 10/2001 | Jordan et al. | |
| 6,325,622 B1 | 12/2001 | Kelly et al. | |
| 6,582,226 B2 | 6/2003 | Jordan et al. | |
| 6,866,505 B2 | 3/2005 | Senini | |
| 6,984,127 B2 | 1/2006 | Lai et al. | |
| 7,014,460 B2 | 3/2006 | Lai et al. | |
| 7,033,170 B2 | 4/2006 | Cordato | |
| 7,033,171 B2 | 4/2006 | Wilkerson | |
| 7,063,531 B2 | 6/2006 | Maijer | |
| 7,094,052 B2 | 8/2006 | Abels et al. | |
| 7,140,876 B2 | 11/2006 | Cinader et al. | |
| 7,354,270 B2 * | 4/2008 | Abolfathi et al. | 433/215 |
| 2002/0172910 A1 * | 11/2002 | Bond | 433/20 |
| 2003/0073052 A1 * | 4/2003 | Yamamoto | 433/20 |
| 2005/0136371 A1 * | 6/2005 | Abolfathi et al. | 433/24 |

FOREIGN PATENT DOCUMENTS

JP            2002209914       *   7/2002

OTHER PUBLICATIONS

Koji Noda, Tooth Movement Limited To Periodontal Ligament Width Using Interrupted Orthodontic Force, Orthodontic Waves 65 (2006), pp. 73-80, Published By Elsevier, May 26, 2006.

* cited by examiner

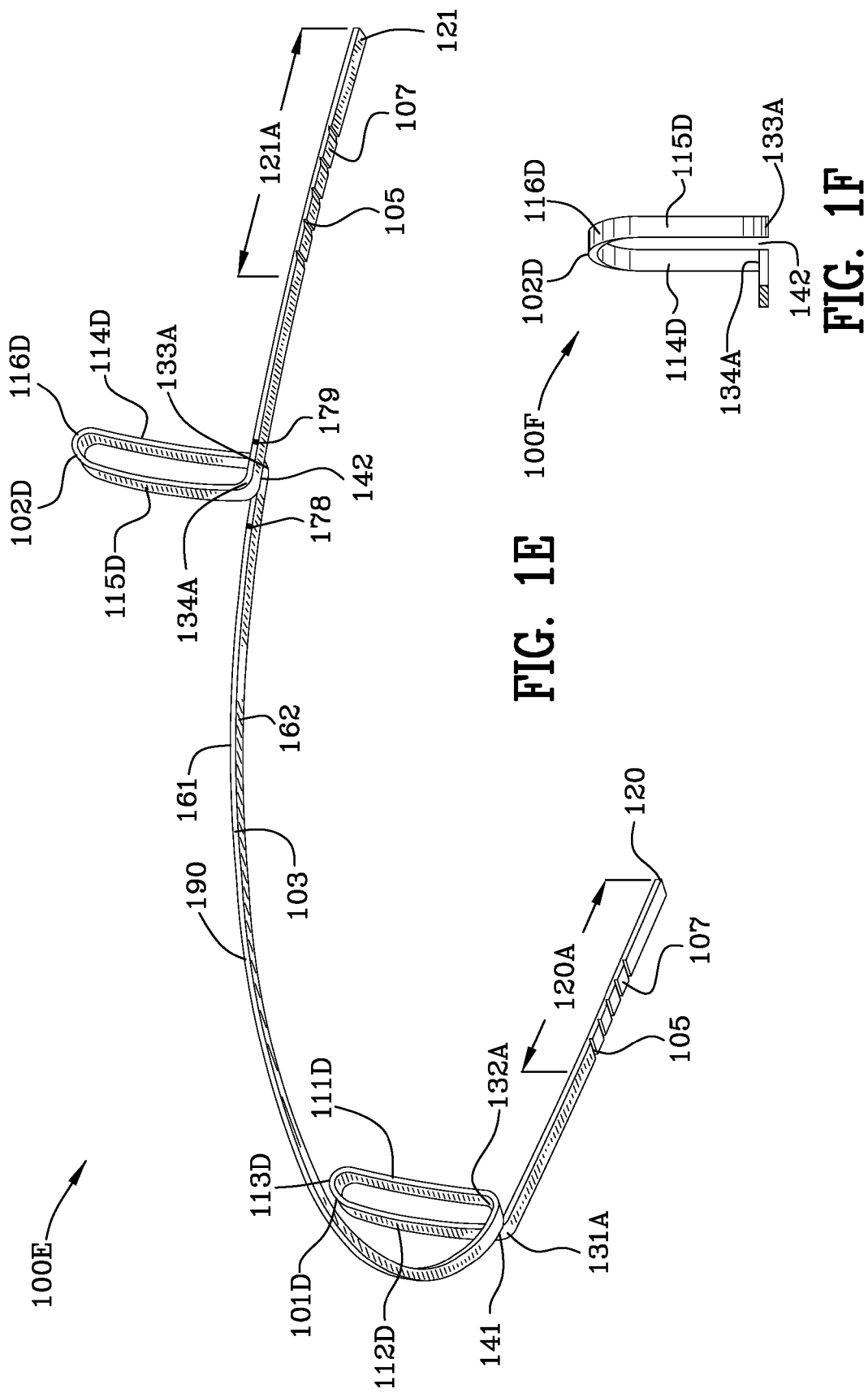

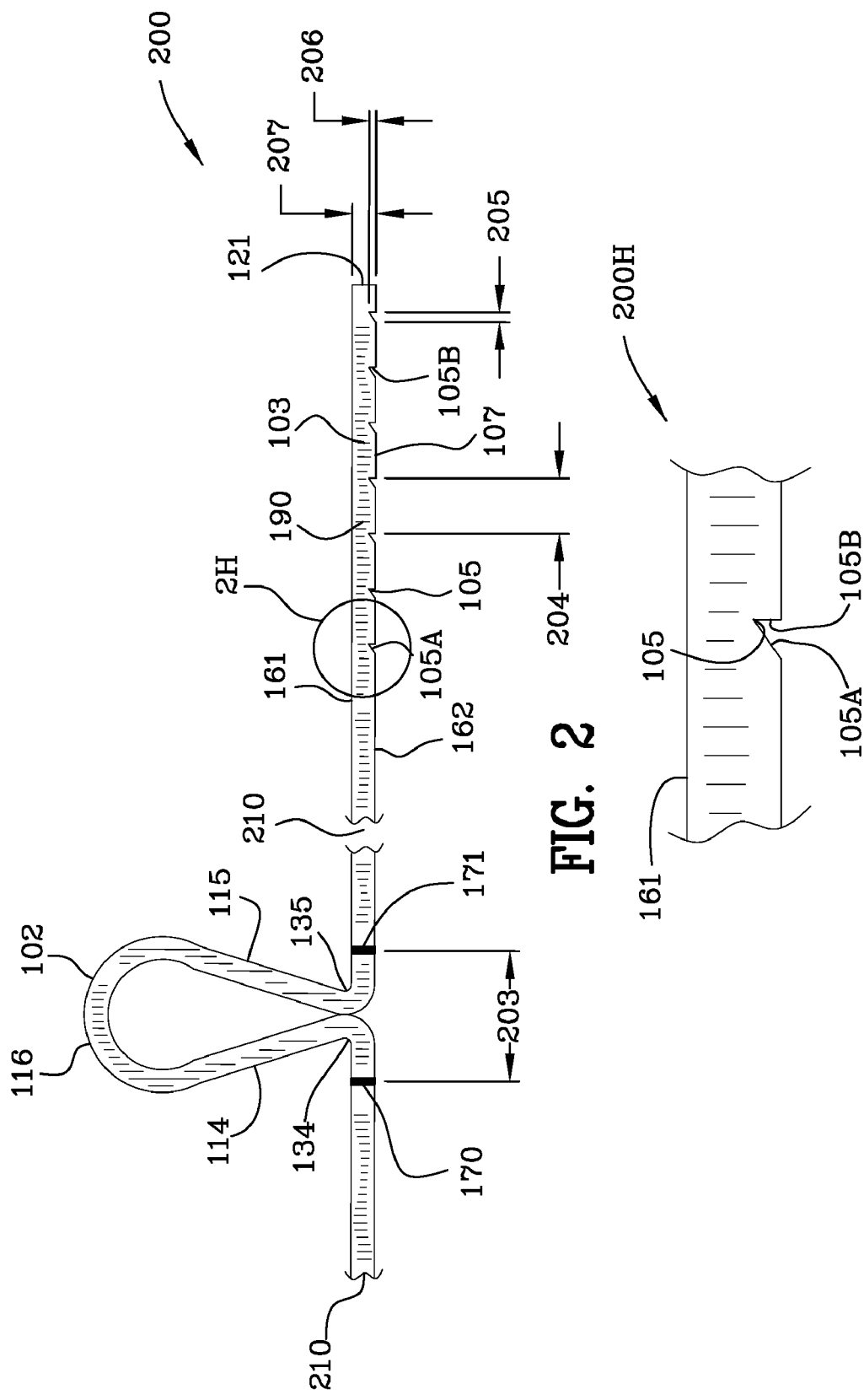

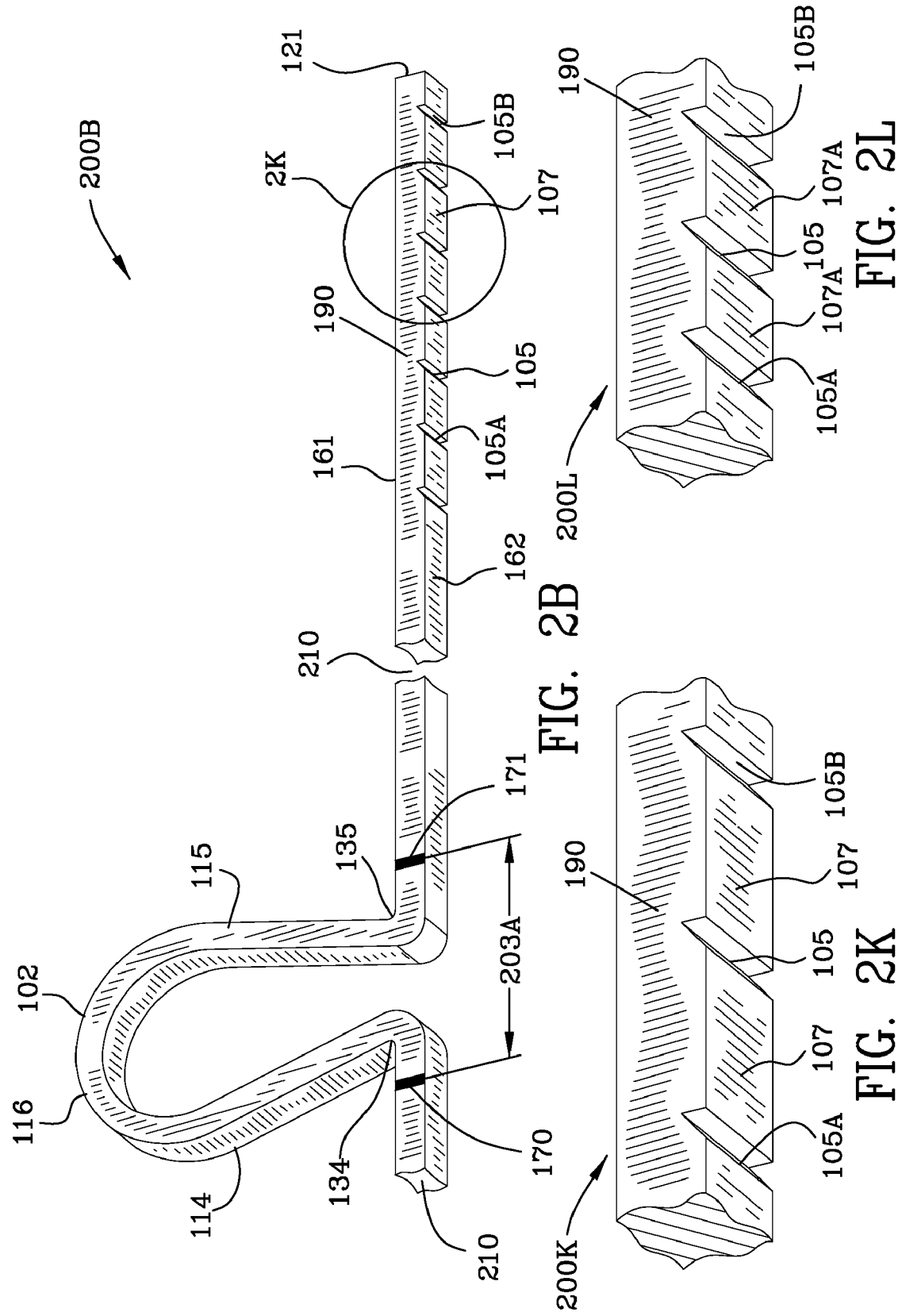

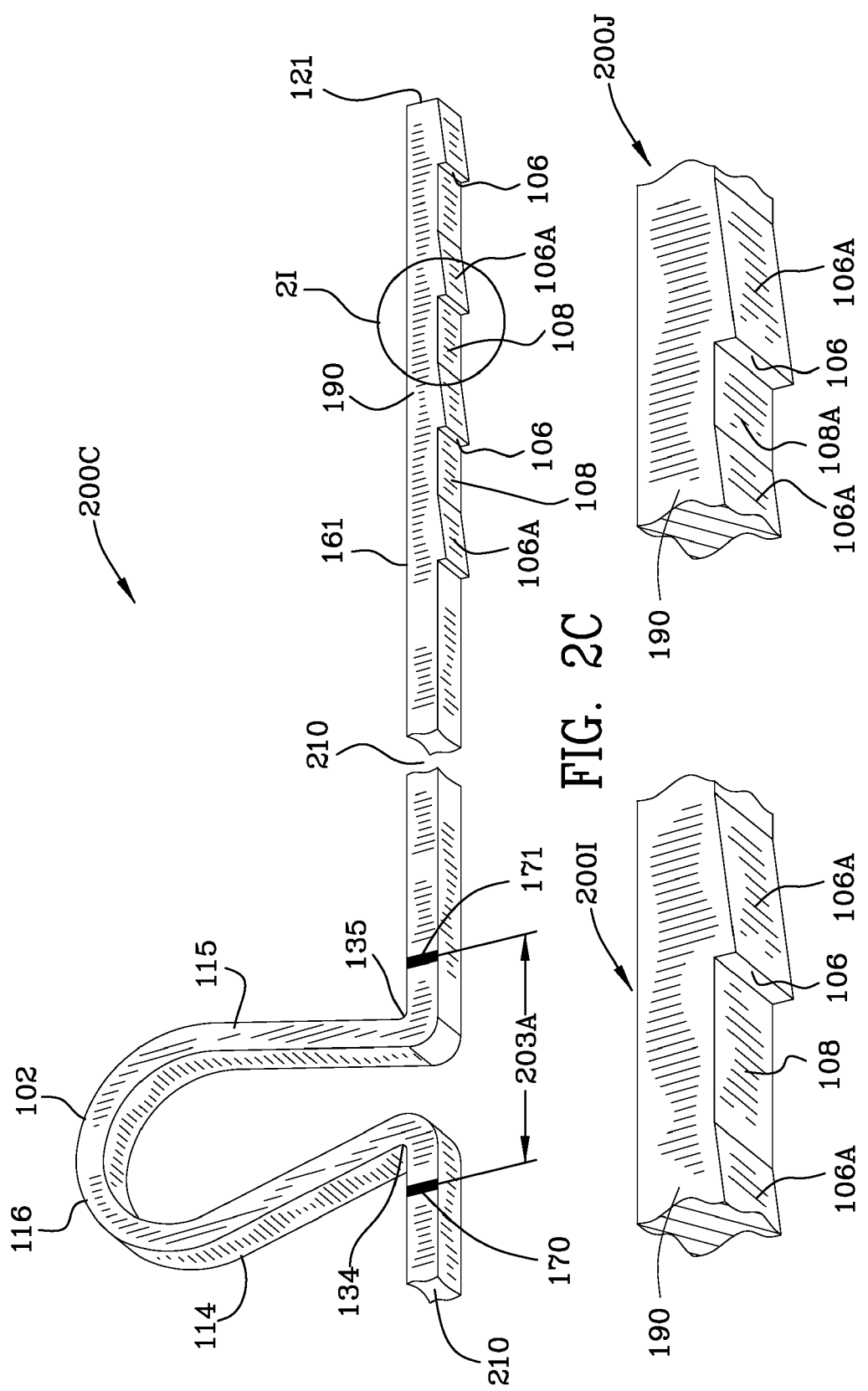

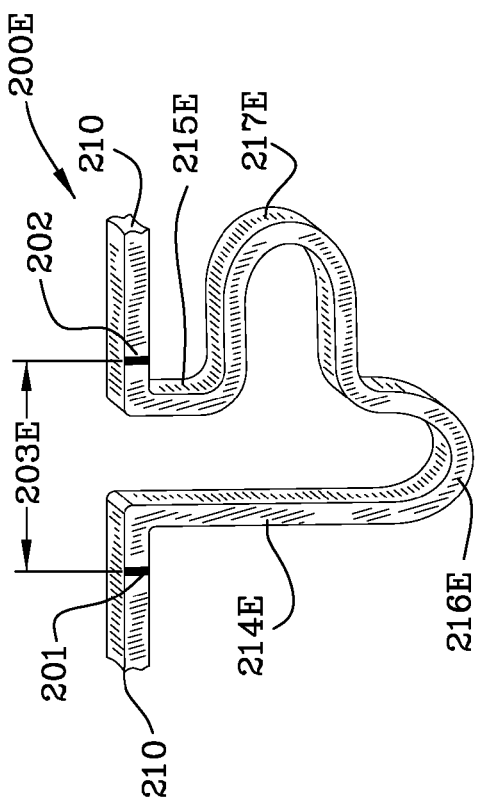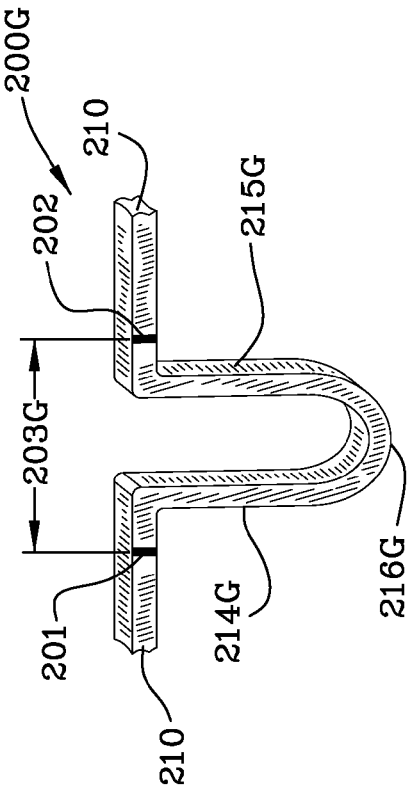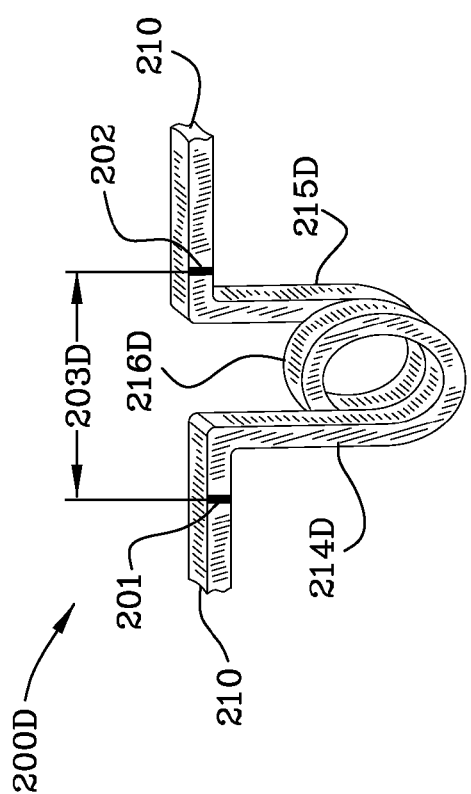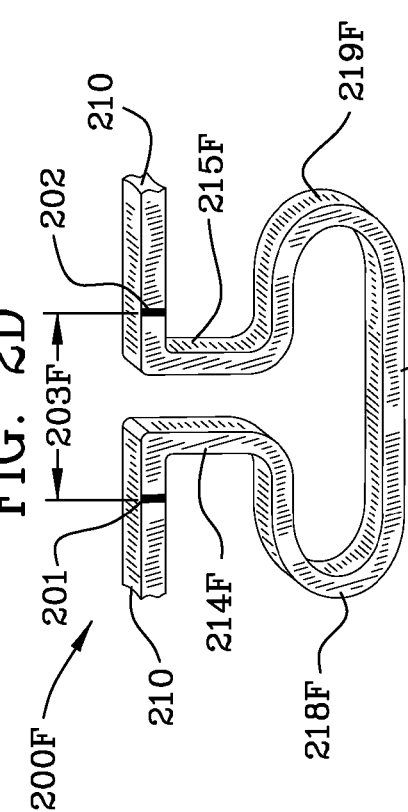

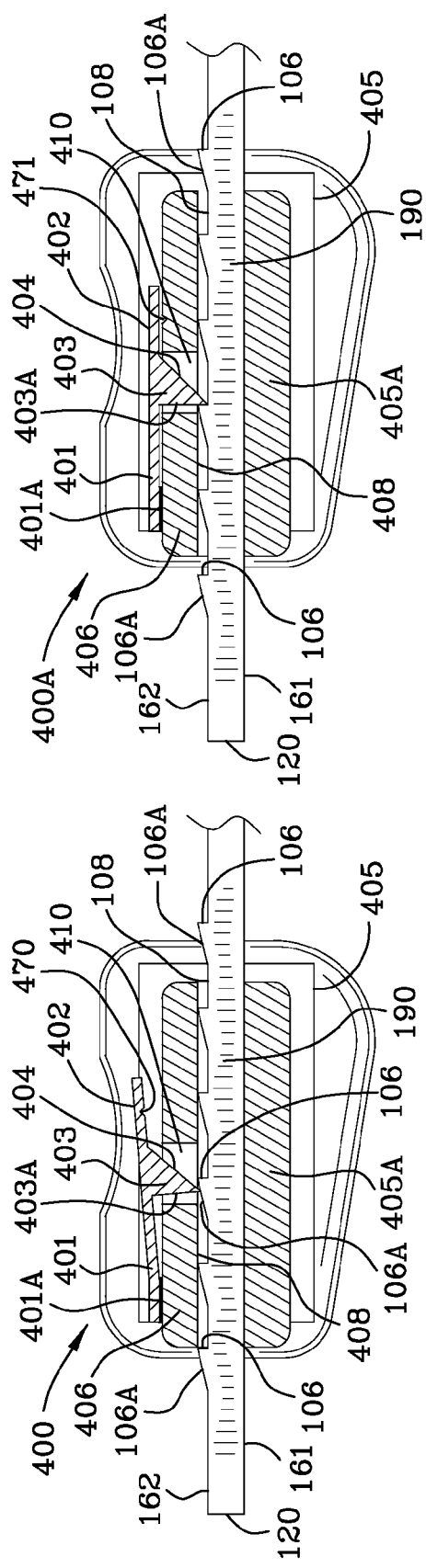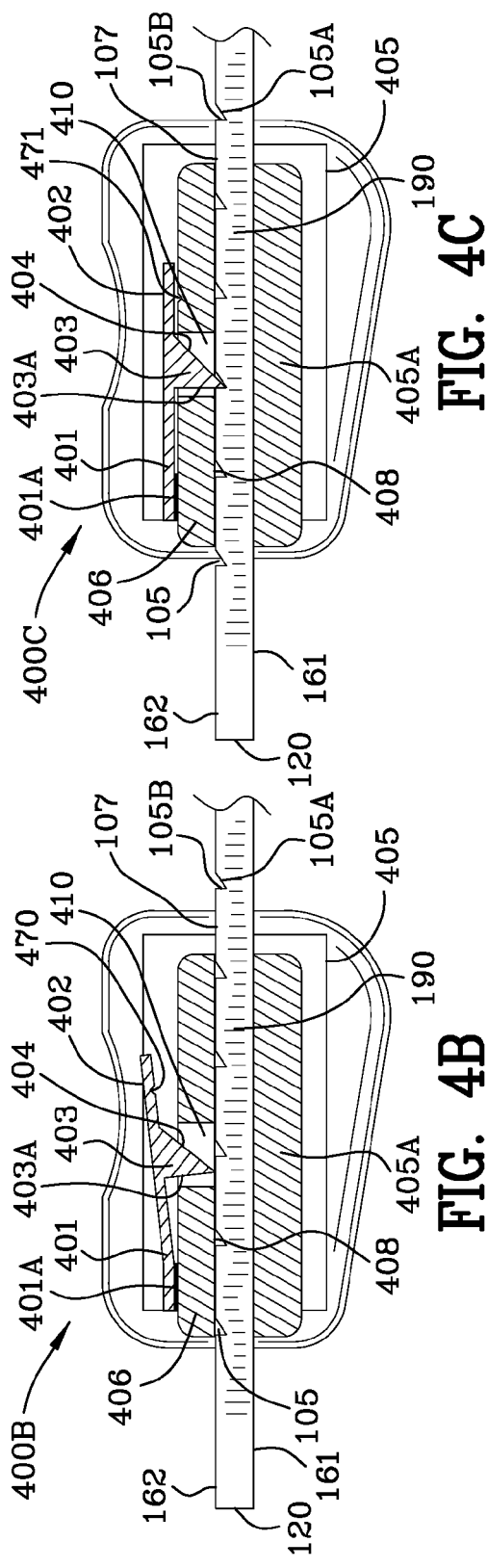

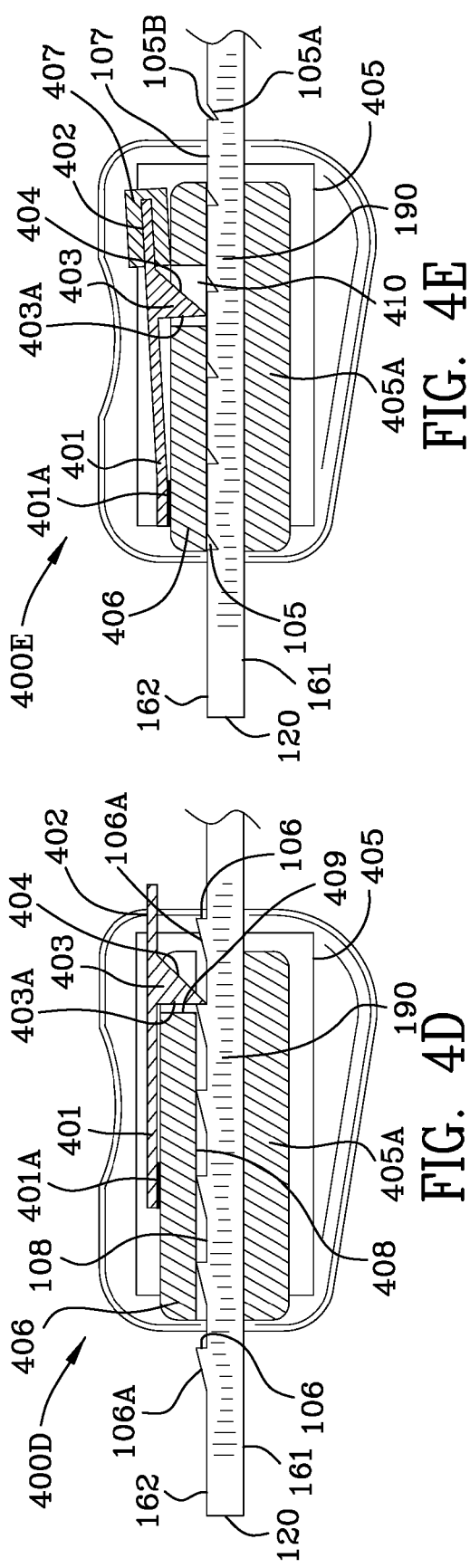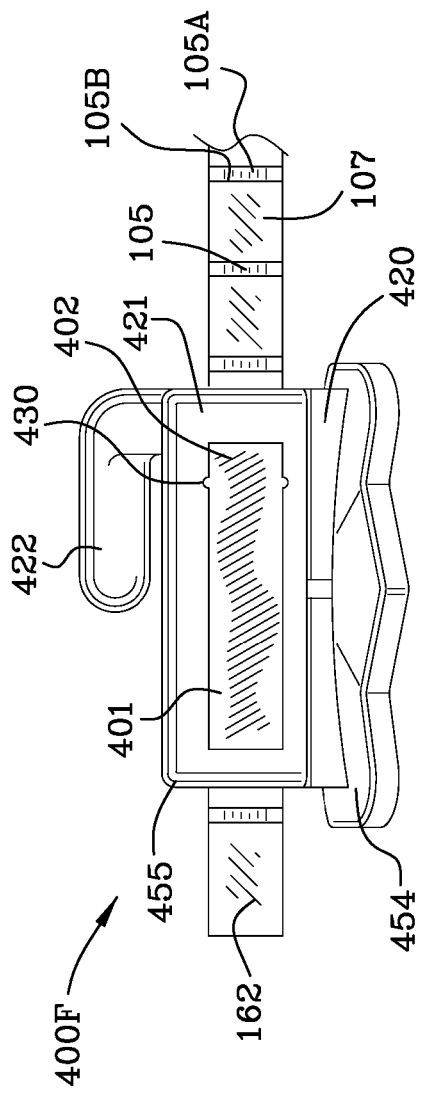

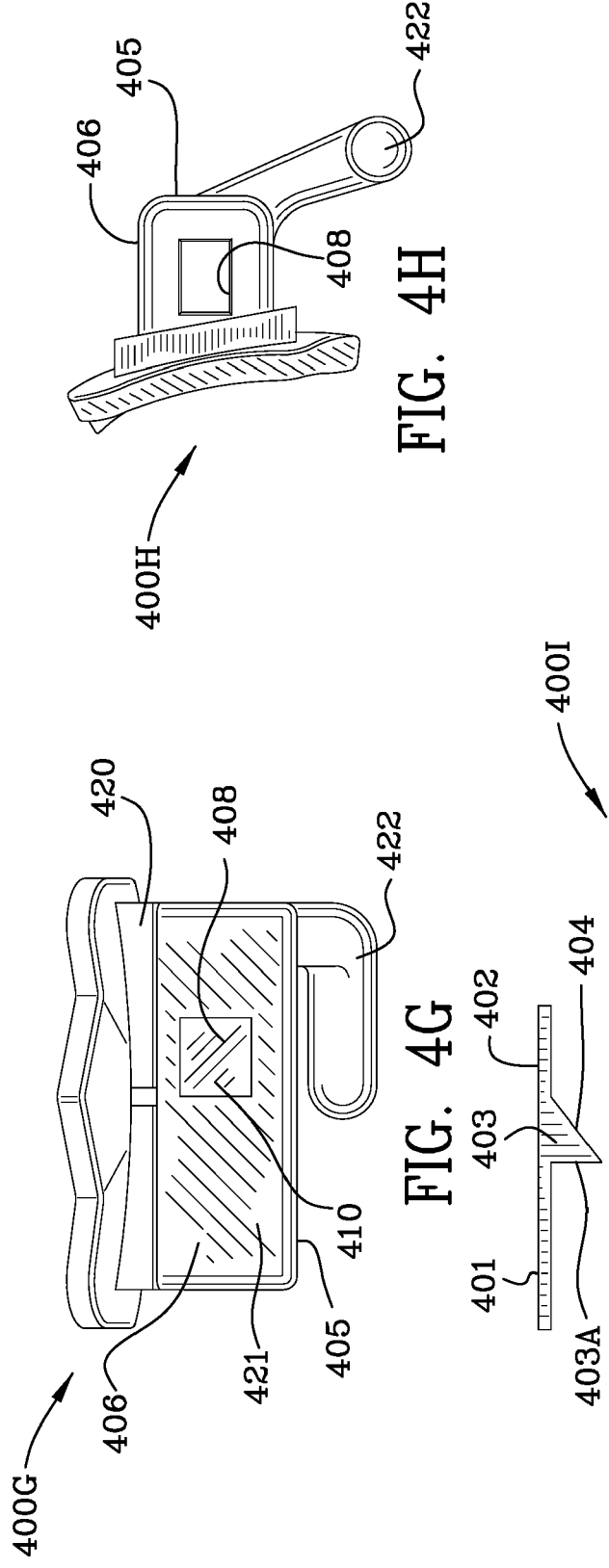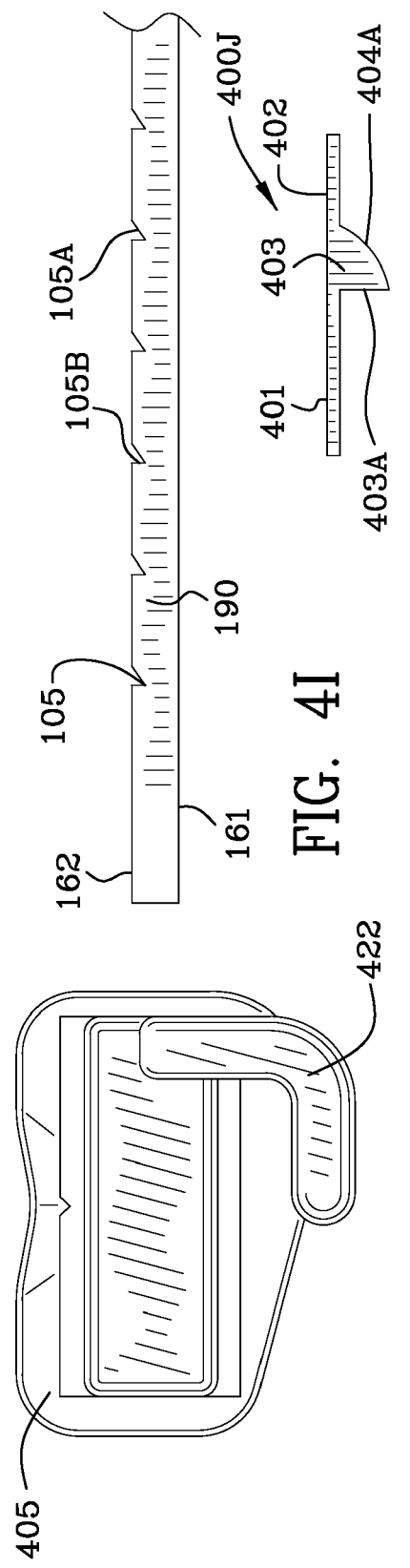

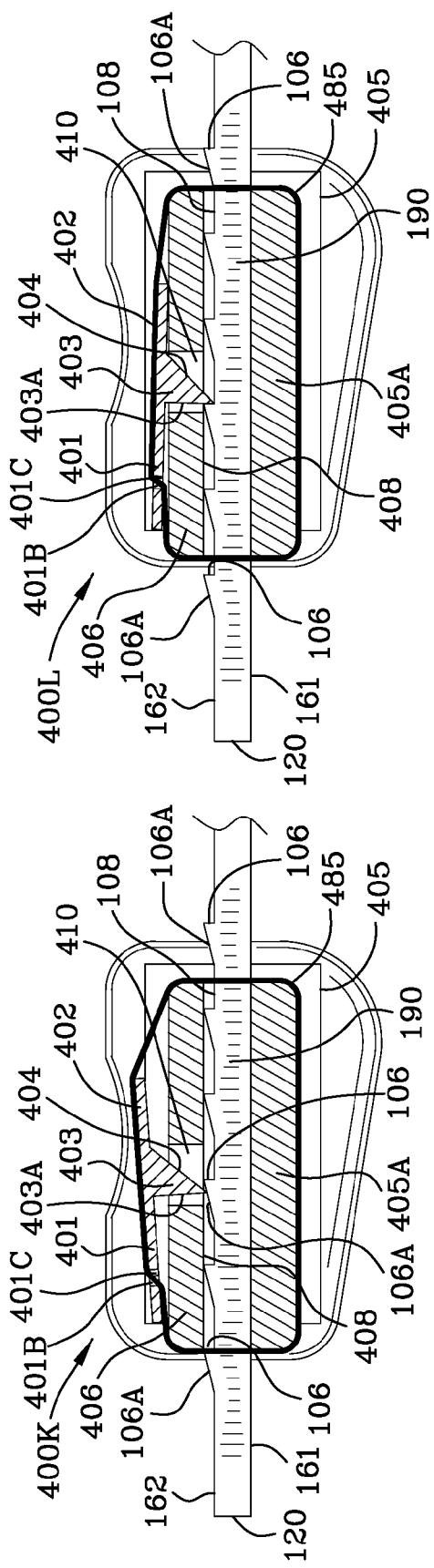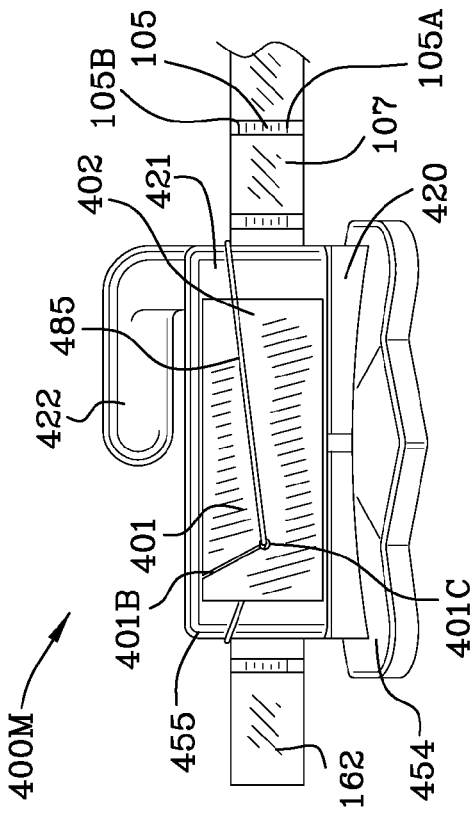

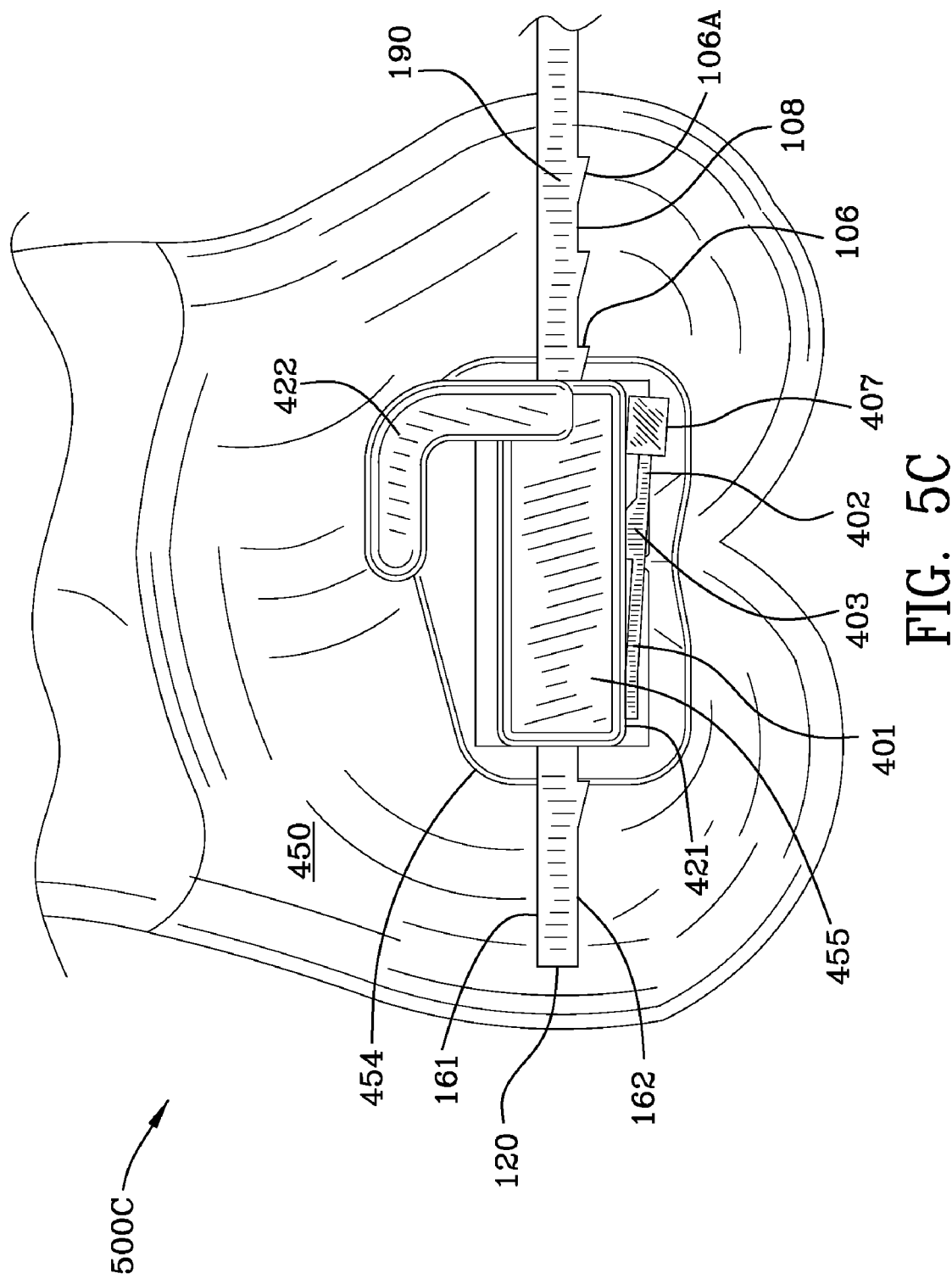

ORTHODONTIC APPARATUS AND METHOD

FIELD OF INVENTION

The present invention relates to the brackets and extendable archwires used in the dental specialty of orthodontics.

BACKGROUND OF INVENTION

U.S. Pat. No. 7,033,171 to Wilkerson discloses, as set forth in the abstract thereof, the following: "[a] molar tube having a first face portion that is adapted to be adhered to a molar tooth, a second face portion, and a mesial-distal length dimension. There is a body portion disposed on the second face portion of the base portion, and the body portion comprises an upper portion and a lower portion. The body portion further comprises a lumen that is adapted to receive an archwire, wherein the lumen has an axis which substantially coincides with the mesial-distal length dimension of the base portion. The body portion further comprises a boss comprising a threaded bore that is adapted to receive a setscrew, wherein the threaded bore has an axis. The axis of the threaded bore intersects with the mesial-distal length dimension to form an angle of any degree between 15 degrees and 55 degrees, including every degree therebetween. A molar tube according to the invention allows for easy adjustment of the tension in an archwire used in an orthodontic dental treatment, and provides for the painless withdrawal of the archwire at any time during or following the treatment." Easy adjustment of the tension as referred to in the '033 patent to Wilkerson requires that the set screw be tightened while tension is applied to the archwire by the orthodontist. Further, in the '033 patent to Wilkerson, no mention is made of measuring the tension in the archwire.

Orthodontics is the specialty of dentistry which focuses on the diagnosis, treatment planning, and treatment of dentoalveolar and skeletal malocclusions. In layman's terms orthodontics broadly and nonspecifically refers to straightening and positioning teeth for the health, comfort, safety and appearance of the patient.

The two major components of fixed orthodontic therapy are tooth attachment mechanisms and archwires. Brackets and bands are used as attachment mechanisms. A band or a bracket may be attached to a tooth, either by cementing or bonding mediums. The purpose of the band or the bracket is to permit the health care provider to transfer a load or force to a tooth or to a group of teeth in order to elicit orthodontic movement of the selected tooth or teeth.

Two issues of concern in orthodontics are friction and management of forces. Although friction may have a positive effect in some instances it is usually associated with detrimental effects. The reason for this is that force which exceeds the ideal force necessary to move a tooth or teeth often must be employed to overcome various forms of friction which are inherent in the biomechanics of sliding mechanics. Thus, the tendency is for sliding mechanics to tax anchorage units (cause undesirable movement of a tooth or teeth that are used in the process of applying forces to a tooth or teeth for which movement is desired).

By contrast, another form of orthodontic biomechanics is referred to as looped mechanics. The "looped" in looped mechanics refers to a variety of shapes of loops which are built into and are an integral part of the archwire when it is constructed. The archwire is passive until the loops are activated. The activated loops act as springs in that they distribute a load through the orthodontic appliances to the tooth or teeth equal to the load of activation.

The load of activation is external to the patient's orthodontic system. Therefore anchorage is not compromised due to friction which is generated when sliding mechanics' techniques are employed for the movement of teeth. Frictional resistance is offset with forces external to the closed orthodontic system without additional energy costs to the closed system.

Orthodontists apply archwires and brackets as follows. First, brackets are attached on one or more teeth. Then the archwire is inserted into the brackets including the molar bracket tubes. The archwire is then ligated to one or more of the brackets. Force (tension) is then applied to the archwire which then opens (activates) or otherwise changes the spring dimensionally which is formed in the archwire. Opening of the spring is also referred to herein as activating the loop spring.

Tension is then applied to the archwire to activate a loop spring.

While forcing the archwire into and through the lumen or passageway of the bracket the orthodontist makes an approximation or educated guess based on experience as to whether or not enough force has been applied to the archwire so as to properly treat the patient. The archwire is then secured by bending it over the rear edge of the bracket to lock it in place.

At least two problems occur with this treatment structure and methodology. First, the locking which takes place by bending the archwire about the end of the bracket may become loose or disengage which then requires readjustment, re-locking or replacement of the archwire. Second, the amount of tension (force) effectively applied to the tooth or teeth is not known. Therefore, more visits to the orthodontist for adjustment and replacement are necessary. Additional visits to the orthodontist using present procedures is costly, inefficient and in some cases creates discomfort for the patient.

Therefore, it is highly desirable for an orthodontist to accurately know the force applied to a tooth or set of teeth. It is further highly desirable for an orthodontist to securely lock the archwire in place and at the same time achieve the desired tension (force). It is further highly desirable to enable the performance of clinical studies wherein the results of the application of a known force can be observed and recorded to assist in future treatment and diagnosis of patients.

SUMMARY OF THE INVENTION

The present invention is directed toward increasing the efficiency of force applications in orthodontics and improving the control and management of the forces. The present invention will additionally improve the ease of controlling and managing the forces.

It is one purpose of the invention to apply a precise load or force to a retraction or protraction archwire. The load or force dissipates as a tooth or teeth move. The invention allows easy retrieval of the retraction or protraction archwire by the health care practitioner.

The application of a load is described hereinbelow.

The orthodontic bracket main body is secured to a base attachable or bonded to the surface of a tooth. The bracket main body may be welded, via the base, to a band attached to the surface of a tooth.

An exemplary embodiment of the invention includes an aperture or opening through an external surface of the bracket which extends through to the internal surface of a bracket tube or slot. This aperture is dimensionally constructed to permit the insertion of a pawl into the tube or slot which when in the active position will permit a calibrated archwire to slide in the desired direction. However, the calibrated archwire is prohibited from sliding in the opposite direction unless the device is deactivated.

Another exemplary embodiment of the invention includes a pawl which is either permanently or removably attached to the orthodontic bracket. The pawl extends into the outer dimension of the bracket slot or tube and allows an extendable archwire to displace the pawl when the wire moves distally. Another exemplary pawl extends beyond the perimeter of the bracket. The pawl includes cam and stop surfaces. When the cam surface is driven by the extendable archwire, the pawl is displaced outwardly.

In another exemplary embodiment of the invention, a portion of the pawl is designed to permit the use of an instrument or other facilitator to disengage the pawl from the extendable archwire. This may be accomplished by mechanically disengaging the pawl from the extendable archwire. This permits the retraction of the pawl extension from the active or engaging position to an inactive or non-engaging position with the use of an instrument or other facilitator and allows the easy removal of the archwire.

An orthodontic device is disclosed and claimed which includes a bracket having a body and the body includes external surfaces. An archwire passageway is formed in the body and extends therethrough. An aperture extends from one of said external surfaces of said body to said passageway. A pawl is attached to the body and includes stop and cam surfaces. The pawl extends into the aperture of the bracket and interengages the archwire.

The extendable archwire includes an adjustment portion having a locking surface and a loop spring therein. The adjustment portion of the extendable archwire is inserted into and through the passageway of the bracket and resides partially in the passageway of the bracket. Notches or protrusions on the archwire interengage the pawl and prevent the extraction of the archwire from the bracket. The adjustment portion of the extendable archwire is selectively movable with respect to and within the passageway of the bracket.

The loop spring in the extendable archwire resists the extension thereof. Upon the application of extension force the loop spring opens resulting in tension in the archwire. The loop under tension is said to be activated. Force is applied to the extendable archwire by the orthodontist, pushing the archwire into and through the bracket and/or by pulling the archwire further out of the bracket once it has been fed into and through the bracket.

Under the forces contemplated herein displacements are manifested by opening of the loop and no significant change in the cross-section of the archwire occurs. Put another way, the strain in the wire is minimal.

Loop springs in the extendable archwire may be in many different forms. It may be an open loop spring, a closed loop spring, a coil loop spring or it may be assume practically any shape.

The loop spring would retract the extendable archwire upon the discontinuation of the application of extension force by the orthodontist. However, the retraction of the archwire is prevented by the interaction of the pawl with the notches and/or the protrusions in the adjustment portion of the archwire.

The pawl of the bracket and the locking surface of the adjustment portion of the extendable archwire form a ratchet. A cam surface of the pawl interengages the extendable archwire as the extendable archwire is extended through the bracket under the application of force to the extendable archwire. Stop surface of the pawl interengages the locking surface of the adjustment portion of the extendable archwire preventing retraction of the extendable archwire upon discontinuation of the application of external force.

A method for using the orthodontic device is also disclosed and claimed. The method includes attaching a bracket to a tooth. The bracket has a passageway therethrough and a pawl extends into the passageway. One end of the extendable archwire having a loop spring is attached to an anchor. The anchor may be a band, ligature or bracket. An adjustment portion of the extendable archwire is inserted into and through the passageway of the bracket. The adjustment portion includes locking surfaces which may reside on notches and/or protrusions.

Force is applied to the extendable archwire which extends the extendable archwire by applying force to the archwire to move the adjustment portion including the locking surfaces distally with respect to the anchor. The anchor may be a band, ligature or bracket or other suitable attachment point including another counteracting ratchet bracket. As force is applied to the extendable archwire, tension results in the archwire as the loop spring activates. Depending on the type of loop spring used, "opening" may not be the correct word for describing the action of the spring. Orthodontists typically describe the action of the spring as "activating" the spring rather than "opening" of the spring. Activating may include opening or closing a loop or imparting a load to a spring device. For instance, if a coil spring is used, the spring would not be opened "per se" but rather it would be unwound against the spring force. The pawl interengages respective ones of the locking surfaces as the adjustment portion is forced through the passageway of the bracket.

The archwire and pawl form a ratchet and secure the archwire wherein the pawl interengages a respective desired one of the locking surfaces and prevents the loop spring from retracting the adjustment portion of the extendable archwire toward the anchor.

The archwire may be constructed from a metal, metal alloy, or non-metal material and may have a plurality of shapes and dimensions so as to maximize its effectiveness and the effectiveness of the pawl.

The archwire of the instant invention encompasses use of Nickel-Titanium alloys. These materials are resilient in character meaning that they considerable flexibility which aids in the treatment of a patient. However, formation of a loop-spring (either open or closed) by a treating orthodontist is difficult because of their resiliency. However, when manufactured loop-springs and indicia may be created and load curves developed. These alloys are very popular in orthodontic practice.

It is an object of the present invention to provide an archwire with a loop spring wherein the loop may be open, closed, and may assume other configurations.

It is an object of the present invention to provide a bracket or tube having an aperture which communicates with a passageway through the bracket.

It is an object of the present invention to provide a bracket with a pawl affixed thereto and an archwire having locking surfaces therein inserted through the bracket such that a ratchet is formed which prohibits retraction of the archwire.

It is an object of the present invention to provide an archwire with reference markings, engravings, or other indicia on the archwire in proximity to a loop spring to measure distances between the marks upon the application of force to open (activate) the loop springs for the purpose of calculating force applied. While the markings, engravings or other indicia are preferred to be in proximity to the loop spring it is specifically contemplated that they may be located remotely from the loop spring or anywhere along the surface of the archwire conducive to the object measurement.

It is an object of the present invention to provide an archwire with locking surfaces in notches and/or protrusions which coact with a pawl to provide proper tension to the teeth of a patient.

It is an object of the present invention to provide a method of applying a desired force to a tooth or teeth of a patient.

It is an object of the present invention to generate a force-extension curve (load curve) for an archwire.

It is an object of the present invention to generate a force-extension curve (load curve) for a plurality of archwires having different geometries made from a variety of materials.

It is an object of the present invention to use indicia which are not necessarily visible to the human eye but which may be identified and measured magnetically or by some other method.

It is an object of the present invention to disengage the pawl from the archwire enabling easy insertion or extraction of the archwire therefrom.

It is an object of the present invention to provide a sheath or some other disengaging apparatus over a portion of the pawl so as to prevent engagement of the pawl with archwire.

It is an object of the present invention to provide a bracket and pawl device which includes a groove in either the pawl or the bracket for inserting a tool for lifting the pawl and allowing the retraction of the pawl so as to release the wire.

It is an object of the present invention to provide a bracket which locks and unlocks an archwire.

These and other objects of the invention will be best understood when reference is made to the Brief Description of the Drawings and the Description of the Invention which follows hereinbelow.

BRIEF DESCRIPTION OF THE DRAWINGS

FIG. 1E is another perspective view of the extendable archwire as illustrated in FIG. 1D.

FIG. 1F is a view taken along the lines 1F-1F of FIG. 1D.

FIG. 2 is an enlarged portion of the extendable archwire of FIG. 1 illustrating one of the unloaded open-loop springs, with somewhat different calibration marks (indicia) located in proximity to the open-loop spring, and adjustment portions of the archwire near the ends of the archwire having notches therein.

FIG. 2B is a perspective view of FIG. 2A.

FIG. 2C is a perspective view of a portion of FIG. 1B illustrating one of the loaded open-loop springs, calibration marks (indicia) located in proximity to the open-loop spring, and an adjustment portion of the archwire near the end of the archwire having protrusions thereon.

FIG. 2D is an example of a loop in the form of a coil spring.

FIG. 2E is an example of a loop wherein one leg includes a loop therein.

FIG. 2F is an example of a loop flattened on the bottom thereof.

FIG. 2G is an example of a loop wherein the legs are spaced apart.

FIG. 2H is an enlargement of a portion of FIG. 2 illustrating one of the notches in the adjustment portion of the extended archwire.

FIG. 2I is an enlargement of a portion of FIG. 2C illustrating one of the protrusions in the adjustment portion of the extended archwire.

FIG. 2J is a view similar to FIG. 2I illustrating an archwire having a land or space between protrusions in the adjustment portion of different length as compared to FIG. 2I.

FIG. 2K is an enlargement of a portion of FIG. 2B illustrating one of the notches in the adjustment portion of the extended archwire.

FIG. 2L is a view similar to FIG. 2K illustrating an archwire having a land or space between notches in the adjustment portion of different length as compared to FIG. 2K.

FIG. 4 is a partial cross-sectional view of an orthodontic molar bracket illustrating an aperture in the occlusal portion, a pawl affixed to the bracket, and an extendable archwire having protrusions thereon inserted through the bracket.

FIG. 4A is partial cross-sectional view of an orthodontic molar bracket similar to FIG. 4 with the stop surface of the pawl engaging the locking surface of a protrusion.

FIG. 4B is a partial cross-sectional view of an orthodontic molar bracket illustrating an aperture in the occlusal portion, a pawl affixed to the bracket, and an extendable archwire having notches therein inserted through the bracket.

FIG. 4C is partial cross-sectional view of an orthodontic molar bracket similar to FIG. 4 with the stop surface of the pawl engaging the locking surface of a notch in the extendable archwire.

FIG. 4D is a partial cross-sectional view of an orthodontic molar bracket wherein the pawl is affixed to the bracket and extends beyond the body of the bracket with the stop surface of the pawl engaging the locking surface of a protrusion.

FIG. 4E is a partial cross-sectional view of an orthodontic molar bracket illustrating an aperture in the occlusal portion, a pawl affixed to the bracket and having a sheath over a portion of the pawl, and an extendable archwire having notches therein inserted through the bracket.

FIG. 4F is a view of an orthodontic molar bracket including the pawl with an extendable archwire therethrough.

FIG. 4G is a view of another orthodontic molar bracket including the aperture for receiving the pawl.

FIG. 4H is a side view of the orthodontic molar bracket illustrating a passageway therethrough.

FIG. 4I is an exploded assembly view illustrating a molar bracket, pawl and extendable archwire.

FIG. 4J is an assembly view illustrating a pawl having a curved ramp.

FIG. 4K is a partial cross-sectional view of an orthodontic molar bracket illustrating an aperture in the occlusal portion, a pawl affixed to the bracket using a ligation device (elastomeric, steel . . . etc.), and an extendable archwire having protrusions thereon inserted through the bracket.

FIG. 4L is partial cross-sectional view of an orthodontic molar bracket similar to FIG. 4 with the stop surface of the pawl engaging the locking surface of a protrusion.

FIG. 4M is a view of an orthodontic molar bracket similar to FIG. 4F including the pawl having slots therein secured to the bracket by more than one ligation or varying patterns of a single ligation device.

FIG. 5C is an enlargement of a bracket applied to a tooth with a sheath over a portion of the pawl.

Figure 1:
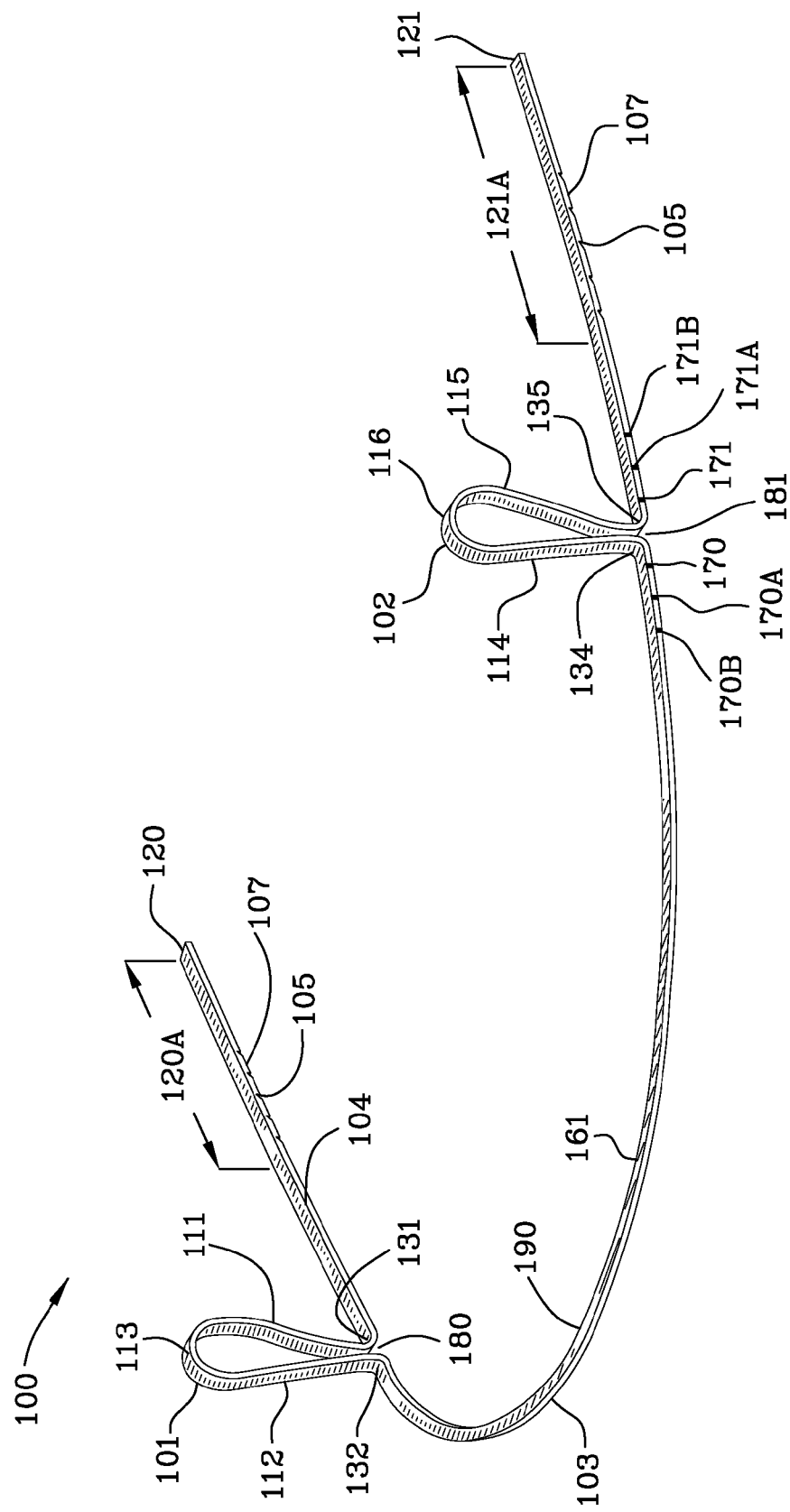
FIG. 1 is a perspective view of an example of an extendable archwire with unloaded open-loop springs, calibration marks (indicia) located in proximity to the open-loop springs, and adjustment portions of the archwire near the ends of the archwire having notches therein.

The drawings will be better understood when reference is made to the Description of the Invention and Claims which follow hereinbelow.

DESCRIPTION OF THE INVENTION

In referring to the drawings hereinbelow the application of a load is described herein without always indicating that a load is applied or showing structure necessary to create the load.

FIG. 1 is a perspective view 100 of an example of an extendable archwire (103, 104, 161, 190) with unloaded open-loop springs 101, 102, calibration marks (indicia) (170, 170A, 170B, 171, 171A, 171B) located in proximity to the open-loop springs, and adjustment portions 120A, 121A of the archwire near the ends 120, 121 of the archwire having notches 105 therein. The first open-loop spring 101 has legs 111, 112 and an intermediate portion 113. Bends 131, 132 in the archwire form the desired loop-spring shape with gap 180 between the legs of the spring.

Second open-loop spring 102 has legs 114, 115 and an intermediate portion 116. Bends 134, 135 in the archwire form the desired loop-spring shape with gap 181 between the legs of the spring.

Deformation of the archwire forms a spring which has a spring constant or spring factor determined as disclosed hereinbelow.

First leg 111 is sometimes referred to herein as the posterior leg of first loop spring 101 and second leg 112 is sometimes referred to herein as the anterior leg 112 of the first loop spring 101. Second leg 114 is sometimes referred to herein as the anterior leg of second open-loop spring 102 and first leg 115 is sometimes referred to herein as the posterior leg of the second open-loop spring 102.

Spaces 107 between notches 105 in the adjustment portions 120A, 121A of the archwire are viewed in FIG. 1. The archwire is sometimes referred to as the extendable archwire herein because the ends 120, 121 of the archwire may be extended through a molar bracket under force opening the springs 101, 102. Although two springs 101, 102 are illustrated in FIG. 1 this invention specifically contemplates the use of one spring or more than two springs.

The archwire material may be stainless steel, nickel titanium, other metal composition or any other material which may form an archwire and it may have various cross-sectional shapes. Loops spring characteristics as desired may be formed in the archwire. Orthodontists may form the loops or they may be formed by the original equipment manufacturer. The invention disclosed herein will enable the orthodontist or the original equipment manufacturer to determine a force-extension curve for archwires having specific spring configurations. The orthodontist may then calculate the force that has been applied to a tooth or to a group of teeth knowing the deflection of the spring upon activation. The equation used to calculate the force may be determined by the supplier of the archwire or it may be determined by the orthodontist.

For instance, the original equipment manufacturer may use a tension meter or other device to measure an applied force by securing one end of an archwire to an immovable anchor and then applying force to the archwire in a direction opposite the anchor and recording the amount of force applied. Simultaneously, the deflection or opening of the spring is recorded by measuring the distance between marks 170, 171 which are inscribed or marked on the archwire about the loops 101, 102. First an initial distance is determined for the unloaded condition. Next, the distance is recorded which corresponds to the force applied to the archwire. In this way a force-deflection curve is generated which enables the orthodontist to know precisely the tension in the loop allowing force applied to the teeth to be estimated with corresponding precision.

Figure 1A:
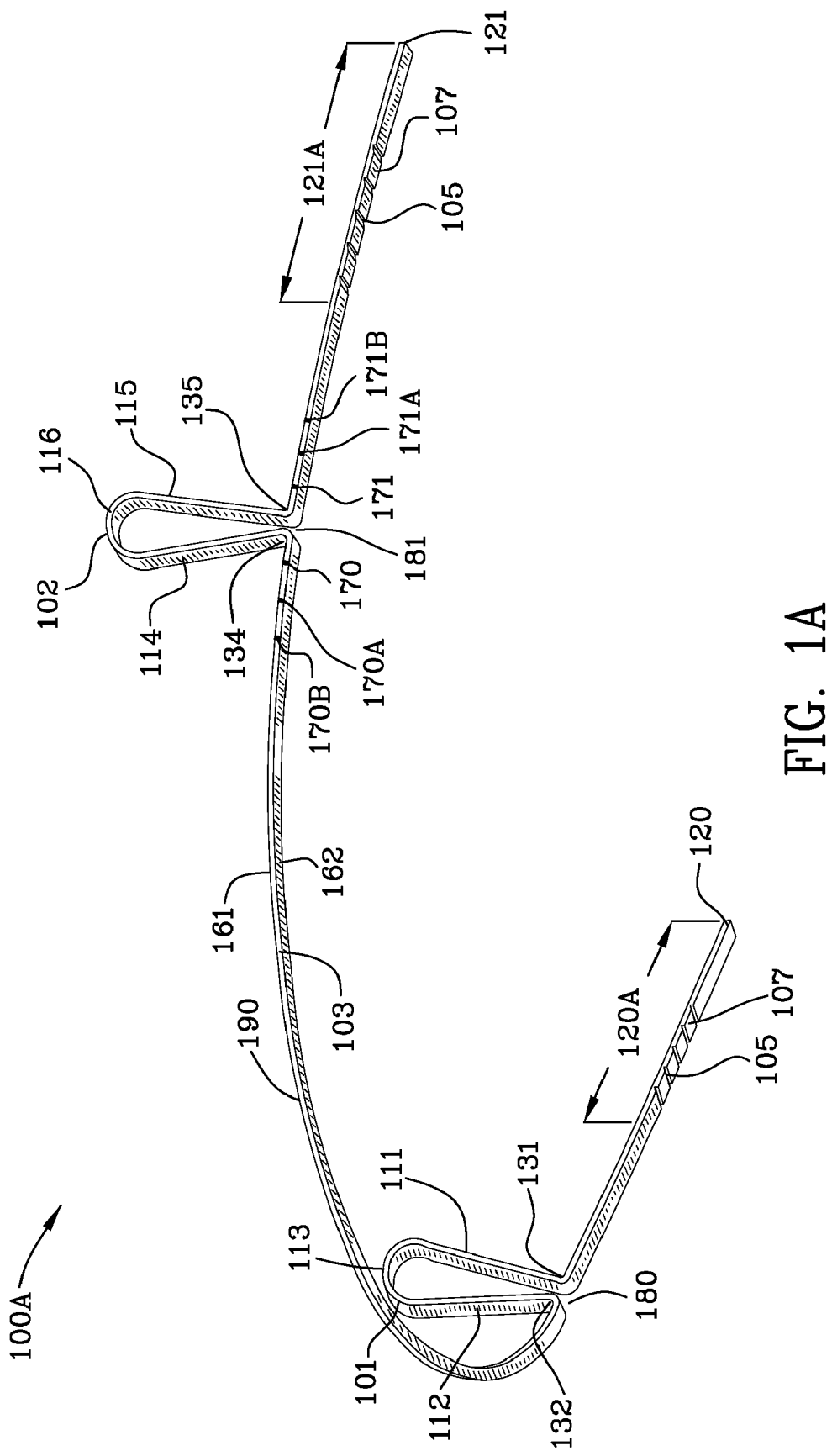
FIG. 1A is another perspective view of the extendable archwire as illustrated in FIG. 1.

FIG. 1A is another perspective view 100A of the extendable archwire as illustrated in FIG. 1. Gaps 180, 181 of loop springs 101, 102 are illustrated well in FIG. 1A. Occlusal side 162 of the archwire is also shown in FIG. 1A and notches 105 are viewed in the archwire as well. By occlusal it is meant to denote the grinding side of the teeth. Notches 105 or protrusions 106 as viewed in other drawings are preferably located on the occlusal side of the archwire so that the orthodontist may access the brackets and adjust the tension (force) in the archwire. For instance, the notches or protrusions may be located on the buccal, gingival, or lingual sides.

Figure 1B:
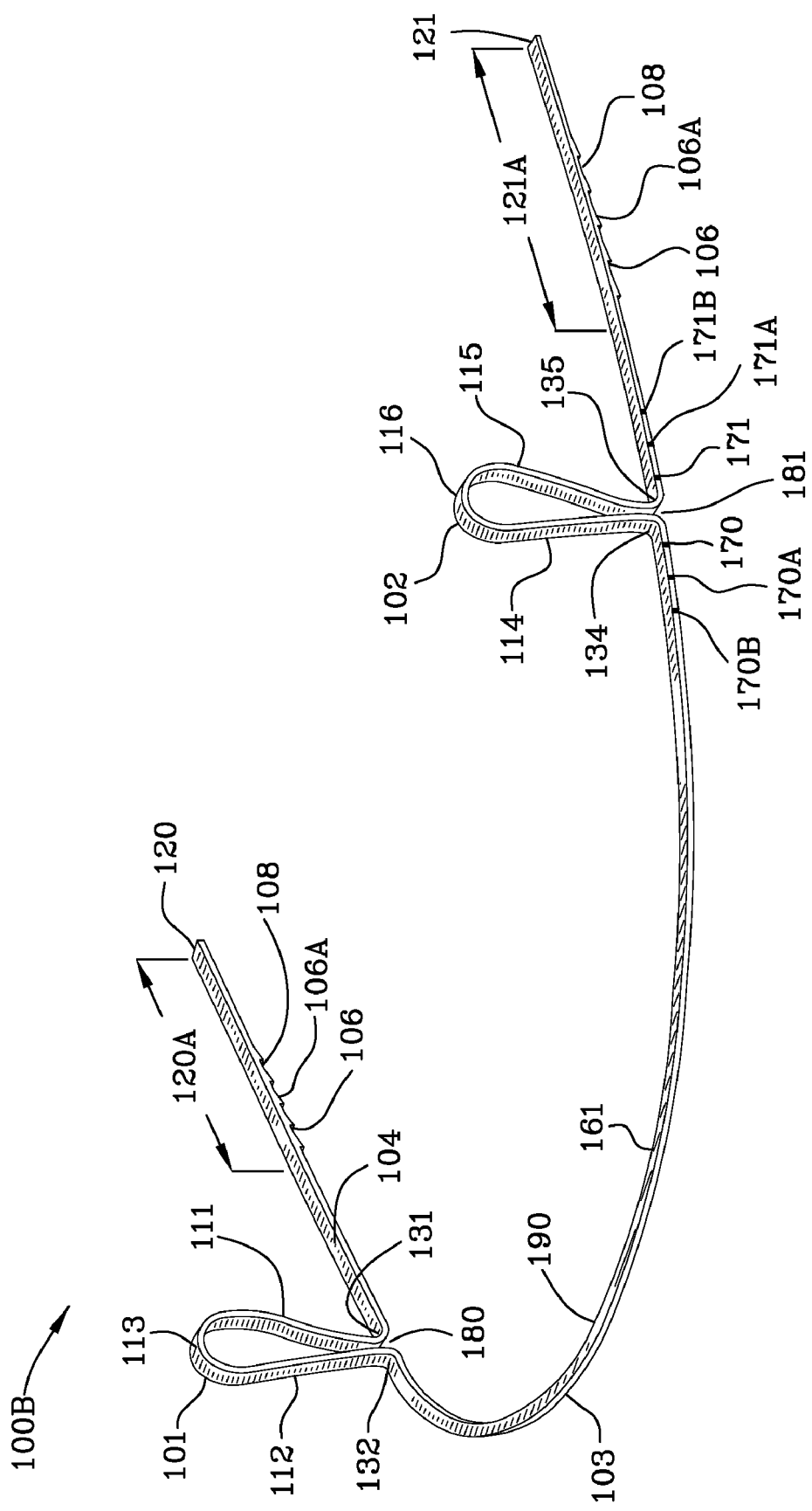
FIG. 1B is a perspective view of an example of an extendable archwire with unloaded open-loop springs, calibration marks (indicia) located in proximity to the open-loop springs, and adjustment portions of the archwire near the ends of the archwire having protrusions thereon.
Figure 1C:
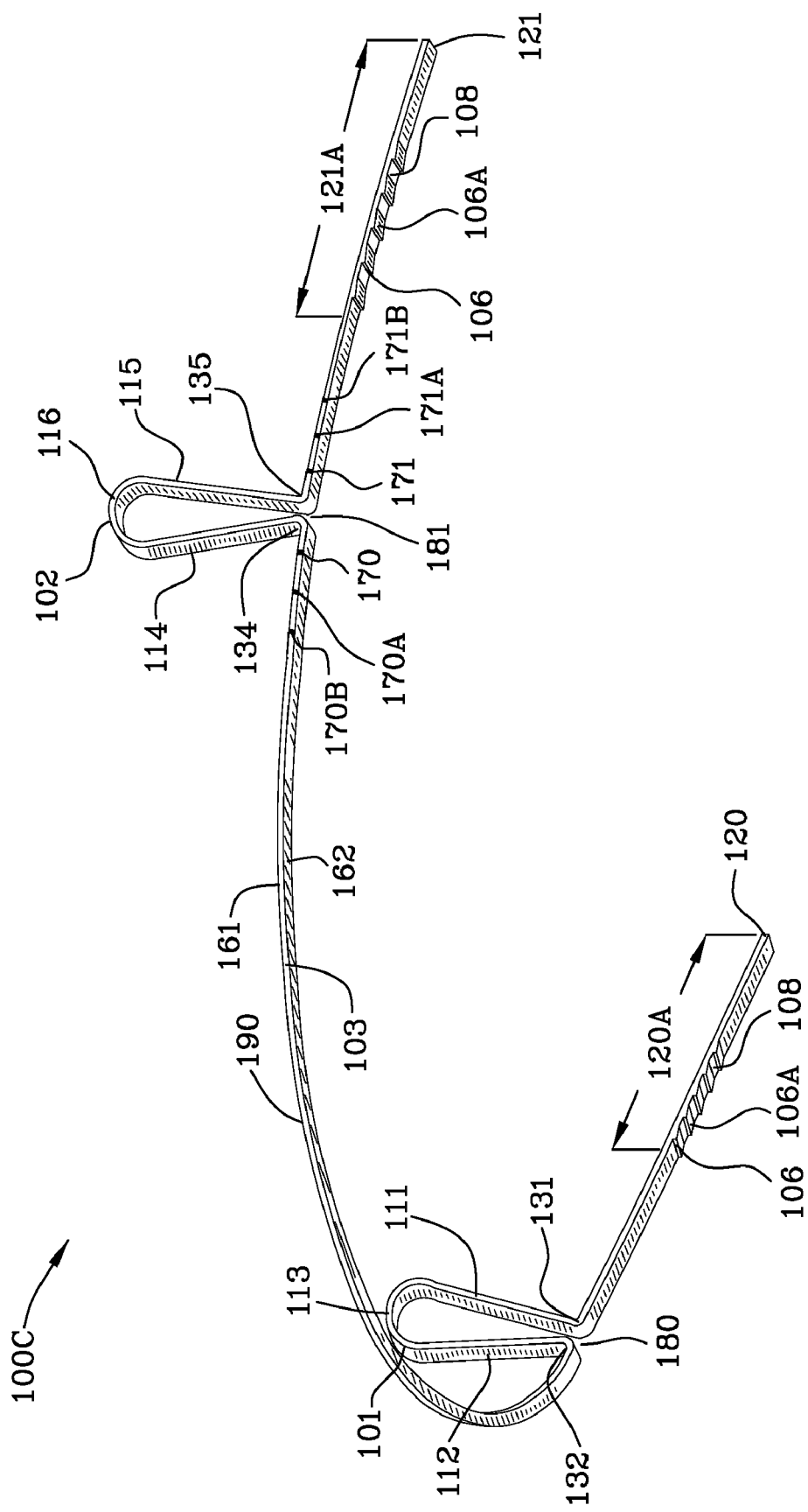
FIG. 1C is another perspective view of the extendable archwire as illustrated in FIG. 1B.

FIG. 1B is a perspective view 100B of an example of an extendable archwire with unloaded open-loop springs 101, 102, calibration marks (indicia) (170, 170A, 170B, 171, 171A, 171B) located in proximity to the open-loop springs, and adjustment portions 120A, 121A of the archwire near the ends of the archwire having protrusions 106, 106A thereon. The adjustment portions 120A, 121A are generally indicated in the drawing figures, however, it is specifically contemplated that the adjustment portions may include a larger portion of the archwire if more locking surfaces or more or different spacing of the locking surfaces are needed or desired. FIG. 1C is another perspective view 100C of the extendable archwire as illustrated in FIG. 1B wherein the protrusions 106, 106A are best illustrated. Space 108 between the protrusions of the adjustment portion of the archwire are also viewed well in FIG. 1C.

Figure 1D:
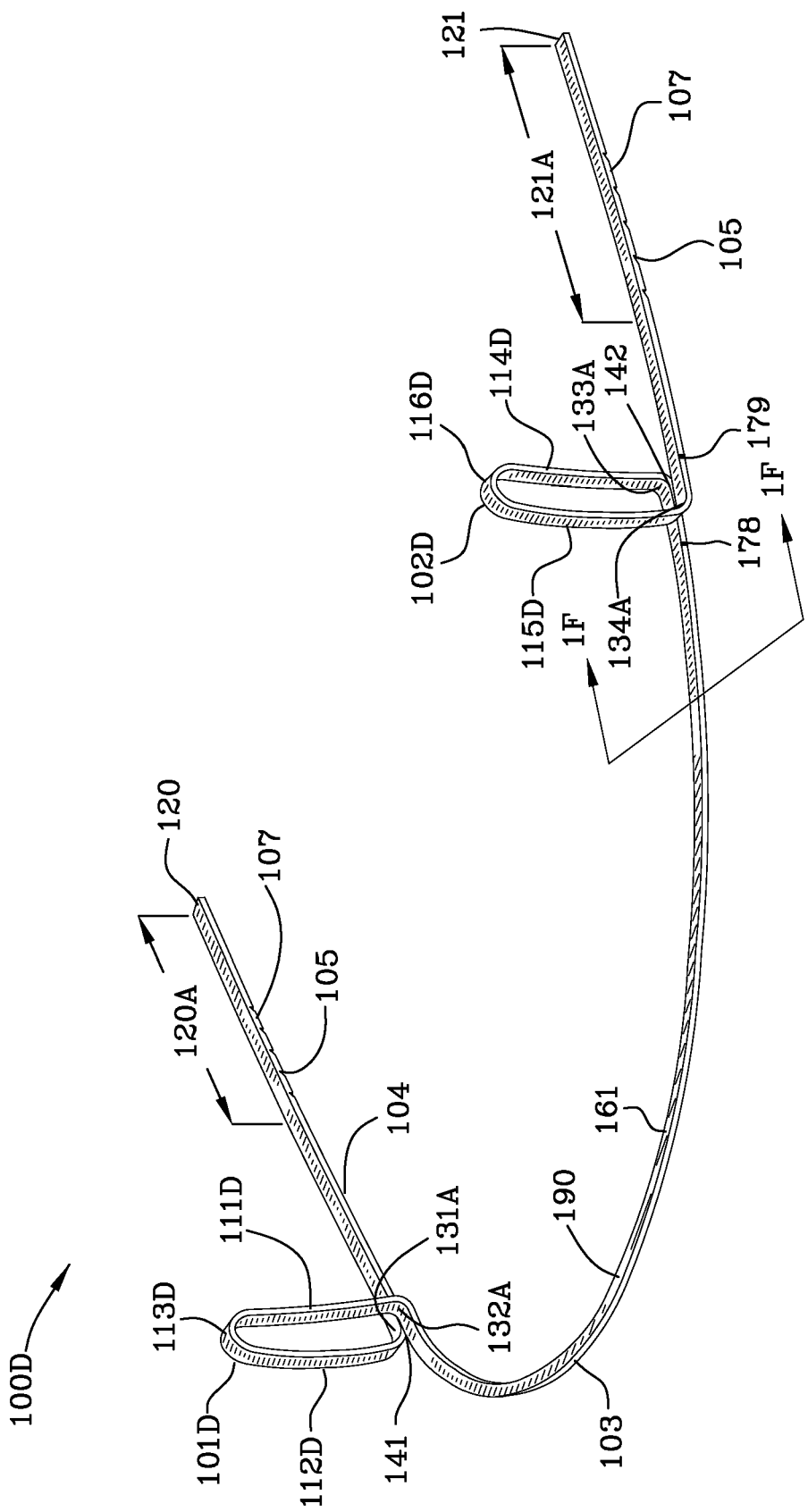
FIG. 1D is a perspective view of an example of an extendable archwire with unloaded offset-loop springs, calibration marks (indicia) located in proximity to the offset-loop springs, and adjustment portions of the archwire near the ends of the archwire having notches therein.

FIG. 1D is a perspective view 100D of an example of an extendable archwire with unloaded offset-loop springs 101D, 102D, calibration marks (indicia) 178, 179 located in proximity to the offset-loop springs, and adjustment portions 120A, 121A of the archwire near the ends of the archwire having notches 105 therein. The offset-loop springs 101D, 102D are sometimes referred to herein as closed-loop springs.

Offset-loop spring 101D includes legs 111D, 112D and intermediate joining portion 113D which joins the legs. Offset-loop 101D includes bending portions 131A, 132A. The legs 111D, 112D are offset and have a gap 141 therebetween.

Offset-loop spring 102D includes legs 114D, 115D and intermediate joining portion 116D which joins the legs. Offset-loop 102D includes bending portions 133A, 134A. The legs 114D, 115D are offset and include a gap 142 therebetween. FIG. 1F is a view 100F taken along the lines 1F-1F of FIG. 1D and illustrates gap 142, legs 114D, 115D, and joining portion 116D.

Figure 1G:
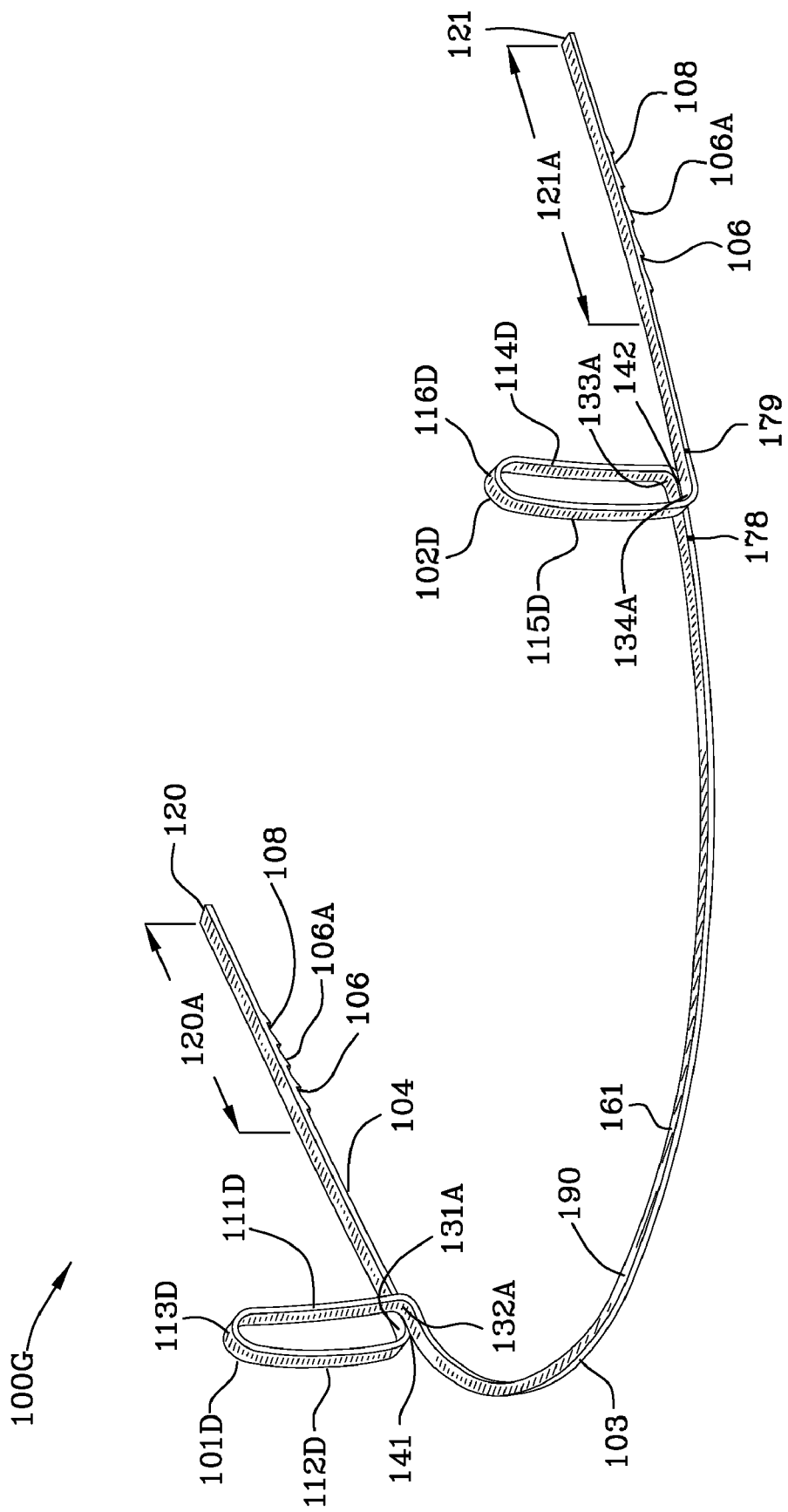
FIG. 1G is a perspective view of an example of an extendable archwire with unloaded offset-loop springs, calibration marks (indicia) located in proximity to the offset-loop springs, and adjustment portions of the archwire near the ends of the archwire having protrusions thereon.
Figure 1H:
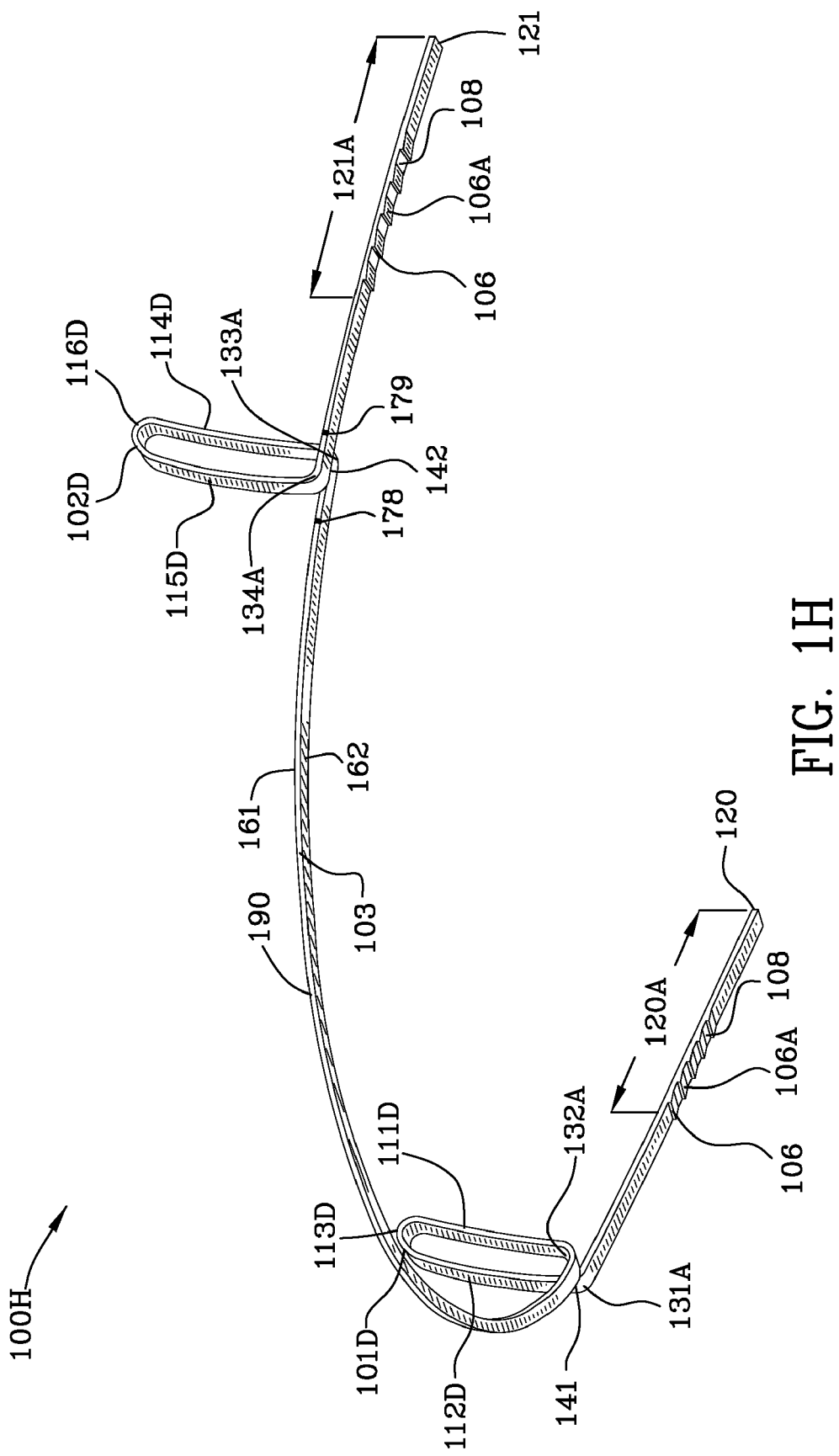
FIG. 1H is another perspective view of the extendable archwire as illustrated in FIG. 1G.

FIG. 1E is another perspective view 100E of the extendable archwire with closed-loops 101D, 102D as illustrated in FIG. 1D. FIG. 1G is a perspective view 100G of an example of an extendable archwire with unloaded offset-loop springs 101D, 102D, calibration marks 178, 179 (indicia) located in proximity to the offset-loop springs, and adjustment portions of the archwire near the ends of the archwire having protrusions 106, 106A thereon. FIG. 1H is another perspective view of the extendable archwire as illustrated in FIG. 1G.

FIG. 2 is an enlarged portion 200 of the extendable archwire of FIG. 1 illustrating one of the unloaded open-loop springs 102, calibration marks (indicia) 170, 171 located in proximity to the open-loop spring, and adjustment portions 121A of the archwire near the end 121 of the archwire having notches 105 therein. Reference numeral 210 represents a discontinuity or break in the archwire so that better resolution in the drawing may be achieved.

FIG. 2H is an enlargement of a portion 200H of FIG. 2 illustrating one of the notches 105 in the adjustment portion of the extended archwire. Notch 105 includes a ramp 105A and a stop face 105B.

Still referring to FIG. 2, reference numeral 203 is the distance between the marks with no load on the archwire. Reference numeral 204 is the distance between the stop faces 105B of the notches. Depth of the notches is indicated by reference numeral 206 and the length of the notch is represented by reference numeral 205.

Different geometry of the notches and their spacing 204 may be used as desired by the orthodontist. For instance, if the notches 105 and their stop faces 105B are spaced closer together then the adjustment of the force associated with each notch is incrementally smaller from notch to notch. This allows the orthodontist to achieve greater control of the force applied to a patient's tooth or teeth. In other words different archwires may be supplied with different notch spacings and with different loop springs providing the orthodontist with a structure and method for better treating a patient. Additionally, the notch depth 206 may be adjusted so as to ensure a larger or more pronounced stop face 105B in the circumstance where a particularly large force is applied to a patient's tooth or teeth. Reference numeral 207 represents the thickness of the archwire in one direction. The archwire may assume any cross-sectional profile and may be round, square, rectangular, triangular or any other polygonal cross-sectional shape. In the situation of the round wire then the notch or protrusion will extend around the circumference of the wire.

The load curves (force-extension curves) which are described herein will be primarily determined by archwire manufacturers. Use of the load curves in conjunction with clinical data will enable more effective treatment of a patient.

FIG. 2D is an example 200D of a loop spring in the form of a coil spring. Indicia 201, 202 is inscribed or painted on the archwire in proximity to the coil spring legs 214D, 215D. Joining portion 216D is a coil which joins the legs 214D, 215D. Reference numeral 203D represents the distance between the legs without the application of force to the archwire.

FIG. 2E is an example 200E of a loop spring wherein one leg includes a loop 217E therein. Legs 214E, 215E and joining portion 216E are all shown in FIG. 2E are marks 201, 202 separated by distance 203E in an unloaded state.

FIG. 2F is an example 200F of a loop spring with an intermediate portion 216F flattened on the bottom thereof. Legs 214F, 215F include portions 218F, 219F which together with joining portion 216F form a generally t-shaped loop spring. Marks 201, 202 are separated by distance 203F in the unloaded state.

FIG. 2G is an example 200G of a loop spring wherein the legs 214G, 215G are joined by intermediate portion 216G and marks 201, 202 are spaced apart by the distance 203G. Those skilled in the art upon reading the disclosure herein will readily recognize that loops having various shapes may be employed in the archwire without departing from the spirit and scope of the claims as set forth herein.

Figure 2A:
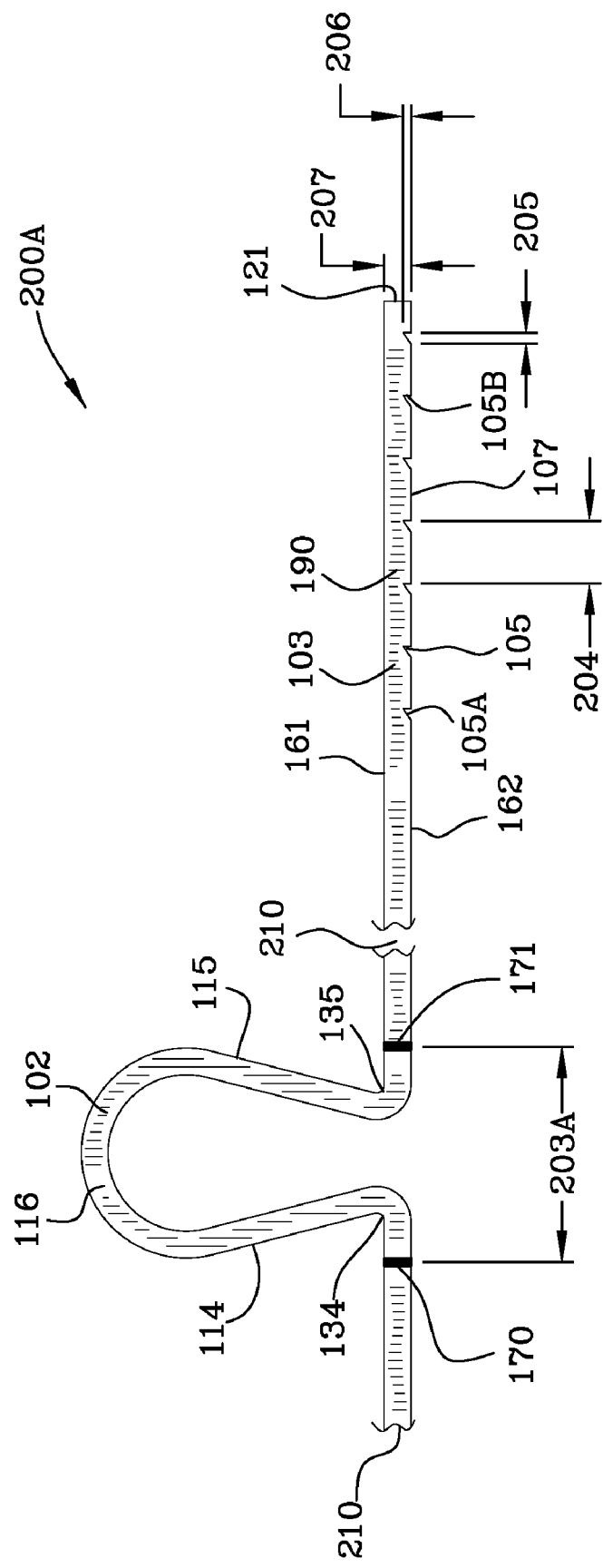
FIG. 2A is an enlarged portion of the extendable archwire similar to FIG. 2 in the loaded state.

FIG. 2A is an enlarged portion 200A of the extendable archwire similar to FIG. 2 in the loaded state illustrating the distance between marks 203A. FIG. 2B is an enlarged portion 200B of the extendable archwire similar to FIG. 2 in the loaded state illustrating the distance between marks 203A and the notches 105 and their stop faces 105B.

FIG. 2C is a perspective view 200C illustrating a loaded open-loop spring 102, calibration marks (indicia) 170, 171 located in proximity to the open-loop spring with a distance 203A therebetween, and an adjustment portion of the archwire near the end of the archwire having protrusions 106, 106A thereon. FIG. 2I is an enlargement 200I of a portion of FIG. 2C illustrating one of the protrusions 106, 106A in the adjustment portion of the extended archwire. Ramp 106A terminates in stop face 106 of the protrusion. Space 108 which of nominal archwire dimension separates the ramp 106A and the stop face 106B of the adjacent protrusion. FIG. 2J is a view 200J similar to FIG. 2I illustrating an archwire having a land or space 108A between protrusions 106, 106A in the adjustment portion 121A of different length as compared to FIG. 2I. When the protrusions are closer together as illustrated in FIG. 2J then the force applied can be adjusted with greater precision as is done when making a vernier (fine) adjustment to an instrument.

FIG. 2K is an enlargement 200K of a portion of FIG. 2B illustrating one of the notches 105 in the adjustment portion 121A of the extended archwire. FIG. 2L is a view 200L similar to FIG. 2K illustrating an archwire having a land or space 107A between protrusions in the adjustment portion 121A of different length as compared to FIG. 2K. When the notches 105 are closer together as illustrated in FIG. 2L then the force applied can be adjusted with greater precision as is done when making a vernier (fine) adjustment to an instrument. In other words the adjustment made in FIG. 2K is somewhat more of a coarse adjustment as compared to the adjustment in FIG. 2L.

Figure 3:
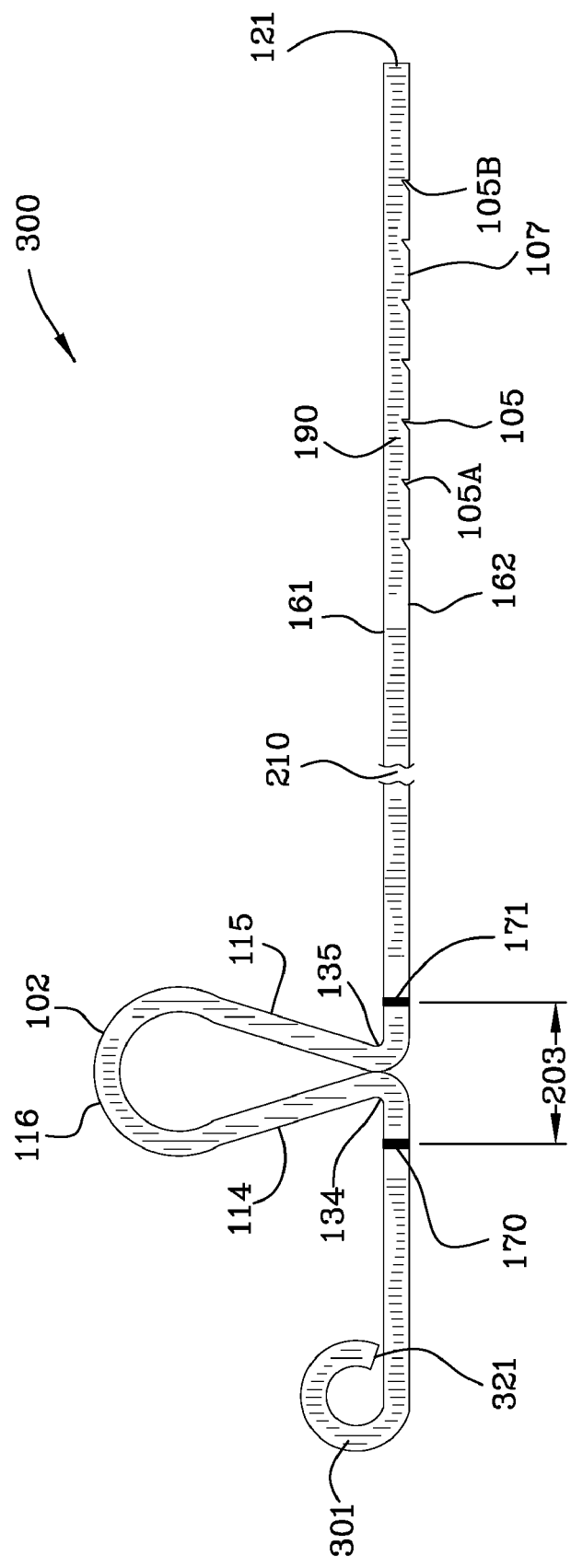
FIG. 3 is a side view of an extendable archwire wherein the archwire is adapted for use with a band, bracket or ligature, with an unloaded open-loop spring, calibration marks (indicia) located in proximity to the open-loop spring, and an adjustment portion of the archwire near the end of the archwire having notches therein.

FIG. 3 is a side view 300 of an extendable archwire wherein the archwire includes a loop 301 is adapted for use with a band, bracket or ligature, with an unloaded open-loop spring 102, calibration marks (indicia) 170, 171 located in proximity to the open-loop spring, and an adjustment portion of the archwire near the end of the archwire having notches therein. FIG. 3B is a perspective view 300B of the extendable archwire 190 of FIG. 3. FIG. 3C is a perspective view 300C similar to FIG. 3B wherein protrusions 106, 106A are used on the extendable archwire and a load is applied.

Figure 3A:
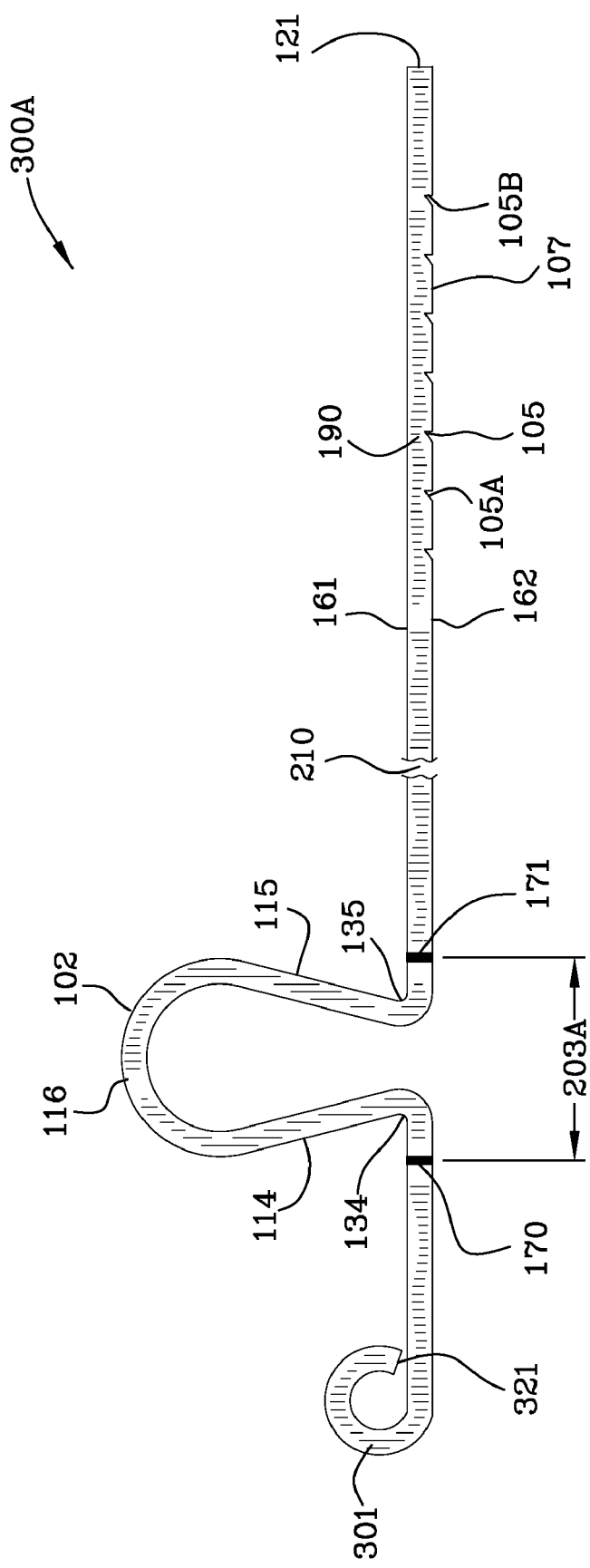
FIG. 3A is a side view of an extendable archwire similar to FIG. 3 with a load applied.
Figure 3B:
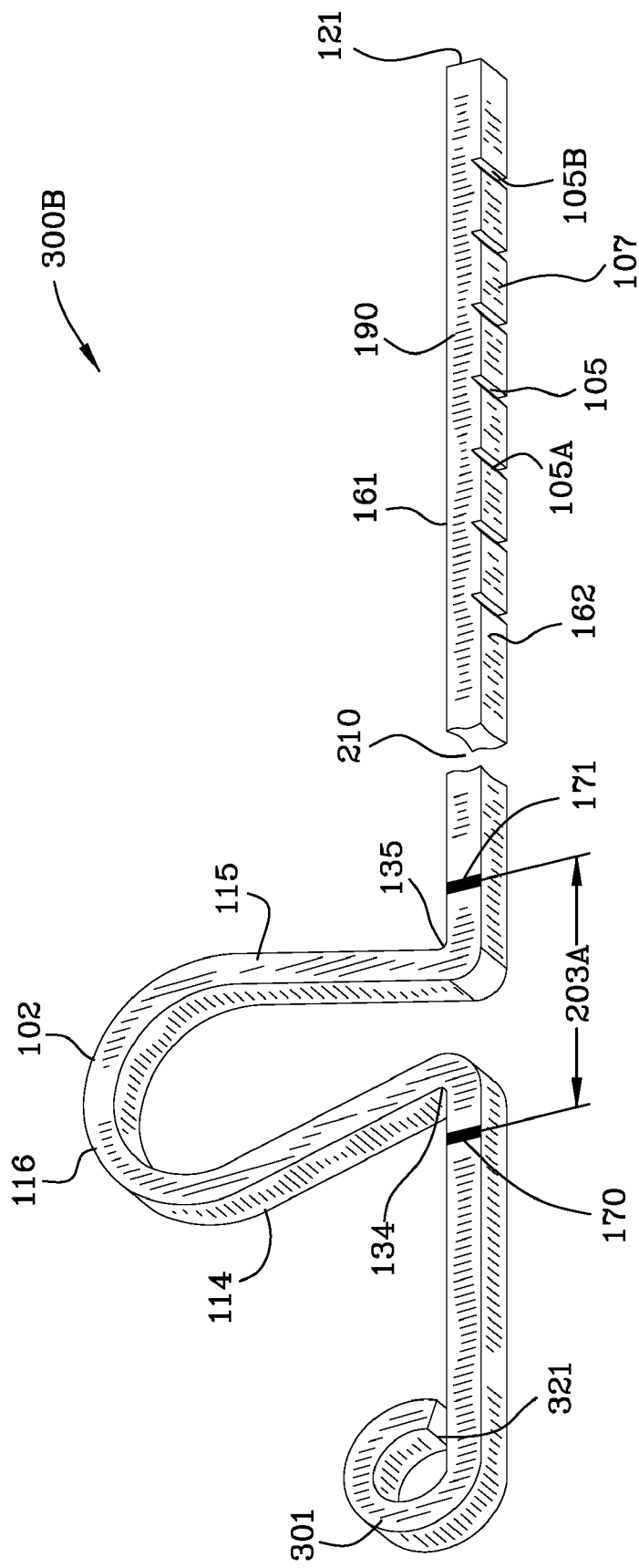
FIG. 3B is a perspective view of the extendable archwire of FIG. 3A.
Figure 3C:
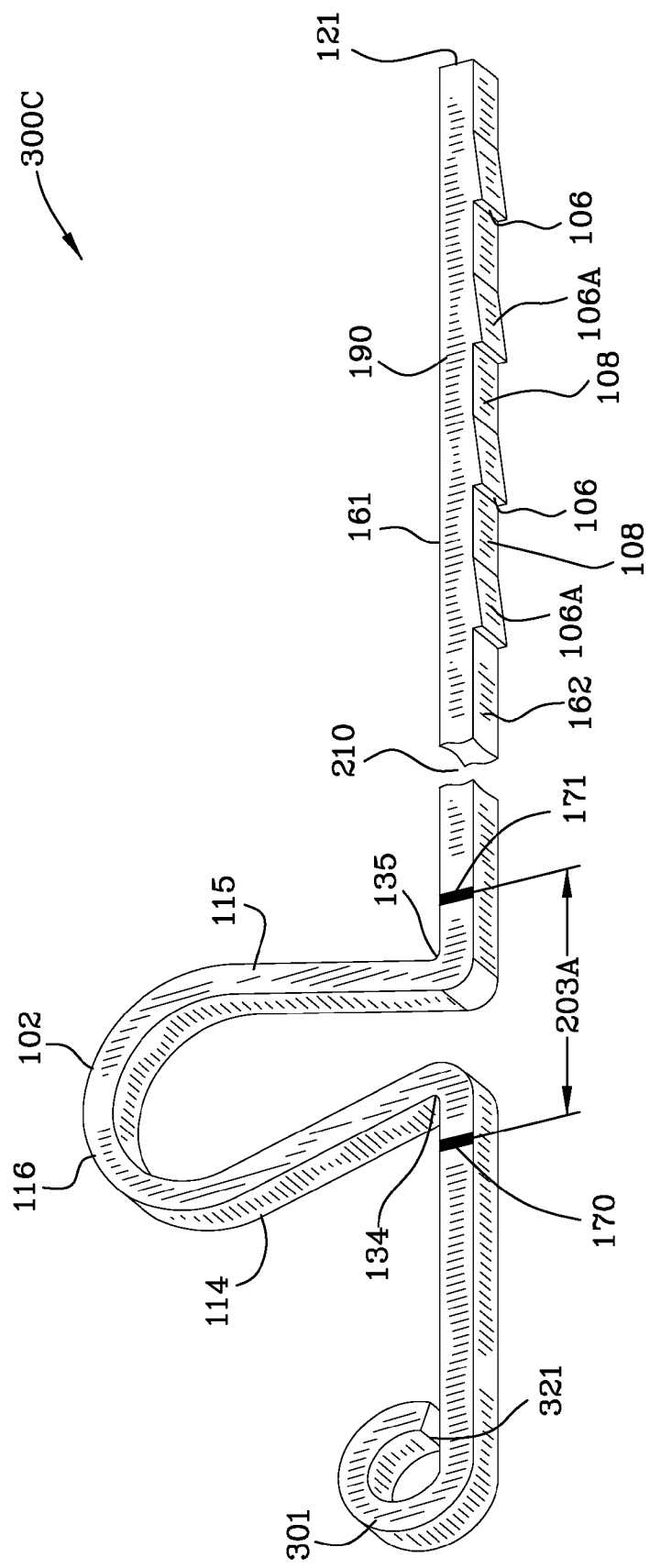
FIG. 3C is a perspective view similar to FIG. 3B wherein protrusions are used on the extendable archwire.

FIG. 3A is a side view 300A of an extendable archwire similar to FIG. 3 with a load applied as indicated by the open loop spring 102 and the indicia 170, 171 and the distance 203A between the indicia.

FIG. 4 is a partial cross-sectional view 400 of an orthodontic molar bracket 405 illustrating an aperture 410 in the occlusal portion or upper portion 406 of the body 405A of the bracket 405. A loop spring 501 such as that shown in FIG. 5A urges the archwire 190 rightwardly when force is applied to the archwire 190 to move it leftwardly. Pawl 403 is affixed to the bracket 405 and an extendable archwire having protrusions 106, 106A thereon is inserted through a passageway 408 of the bracket. Pawl 403 includes a cam 404 and a stop surface 403A.

Referring to FIGS. 4 and 4F, pawl 403 includes an arm 401 which is affixed 401A by welding, soldering, ligation or adhesive to the upper surface 421 of the bracket 405.

Extension arm 402 of the pawl extends past the aperture 410 in the upper portion 406 of the body 405A of the bracket. FIG. 4 illustrates the pawl 403 engaging ramp 106A of the protrusion. In this condition a force (not shown) is urging the archwire leftwardly. This force is created by the orthodontist by pushing or pulling the archwire 190 through the lumen or passageway 408. In the condition as illustrated in FIG. 4 the archwire 190 is not locked and may move rightwardly upon the discontinuation of force until pawl stop surface 403A engages the locking surface 106 on the next adjacent protrusion.

Still referring to FIG. 4, the pawl cam surface 404 and the apex of the pawl cam surface 404 and the pawl stop surface 403A interengage the occlusal side 162 of the archwire and, in particular, the adjustment portion 120A of the archwire which includes the protrusion locking surface 106, protrusion ramp surface 106A and the space 108 between the ramp and locking surfaces. It will be noted that one geometry of the cam surface 403A has been shown by way of example. However, it is specifically contemplated that other cam geometry can be used. For instance a non-linear pawl cam geometry may be used.

FIG. 4A is partial cross-sectional view 400A of an orthodontic molar bracket 405 similar to FIG. 4 with the pawl stop surface 403A engaging the locking surface 106 of a protrusion. In this condition the archwire is free to move leftwardly under force against the loop spring (not shown) but the archwire 190 may not move rightwardly.

FIG. 4B is a partial cross-sectional view 400B of an orthodontic molar bracket 405 illustrating an aperture 410 in the occlusal portion, a pawl affixed to the bracket, and an extendable archwire having notches 105 therein inserted through the bracket. FIG. 4B is similar to FIGS. 4 and 4A except that the archwire 190 includes an adjustment portion having notches 105. As shown in FIG. 4B, the apex of the pawl 403 engages the occlusal side 162 of the archwire 190. The archwire 190 is free to move rightwardly upon the discontinuation of force to urge the archwire leftwardly.

Depending on the length of the archwire 190 and of the adjustment portion, the adjustment portion 120A may be inserted into the lumen 408 and reside there without the application of force by orthodontist and without the application of force by the loop spring. This condition or state just described is also applicable to FIGS. 4, 4A, and 4C.

Referring to FIGS. 4 and 4B, pawl arm 401 will bend as the apex of the pawl rides along the occlusal side 162 of the adjustment portion of the archwire 190. Arm 401 can be made of variety of materials including stainless steel or plastics and has sufficient flexibility and resilience to follow the contour of the archwire and to lock the pawl stop surface 403A against the locking surfaces 105B and 106. Other metal alloys or non-metallic materials may be used.

Still referring to FIGS. 4 and 4A, reference numeral 470 represents a notch in pawl 403 into which a tool may be inserted to allow the raising of the pawl so as to retract the archwire from the bracket. Alternatively, reference numeral 471 represents a notch in body 406 into which a tool may be inserted to allow the raising of the pawl.

FIG. 4C is partial cross-sectional view 400C of an orthodontic molar bracket similar to FIG. 4 with the stop surface of the pawl 403A engaging the locking surface 105B of a notch 105 in the extendable archwire. FIG. 4C is similar to FIG. 4A in operation and effect. Namely, archwire 190 may be forcefully urged leftwardly against the spring 501 (not shown).

FIG. 4D is a partial cross-sectional view 400D of an orthodontic molar bracket wherein the pawl 403 is affixed to the bracket and extends beyond the end 409 of the upper portion 406 of the body of the bracket with the stop surface of the pawl 403A engaging the locking surface 106 of a protrusion. The example of FIG. 4D offers access to the orthodontist of the extension arm 402 for releasing the archwire from the bracket. It will be noticed when reference is made to FIG. 4D that the pawl 403 is attached to the upper portion of the body 406 a considerably longer distance than that illustrated in FIGS. 4A-C and thus the amount of bending of the pawl arm 401 is reduced.

FIG. 4E is a partial cross-sectional view 400E of an orthodontic molar bracket 405 illustrating an aperture in the occlusal portion of the upper body 406 of the bracket 405A. A pawl 403 is affixed to the bracket and a sheath 407 resides over a portion of the pawl. As in the examples of FIGS. 4-4D, an extendable archwire 190 having notches therein has been inserted through the bracket.

Figure 5:
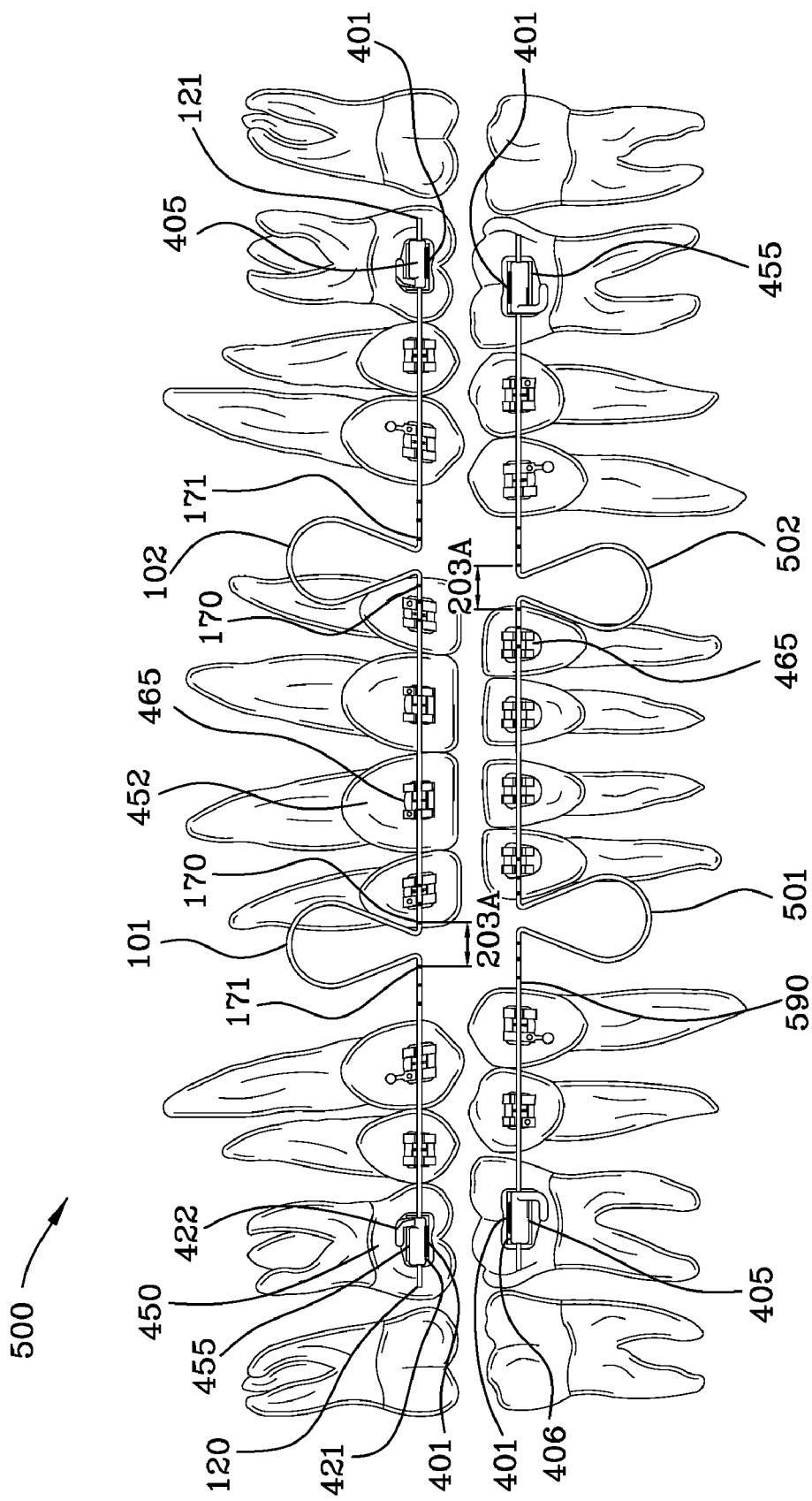
FIG. 5 is an orthographic projection of the orthodontic device applied to a patient's teeth with load applied and the loop-springs activated.
Figure 5A:
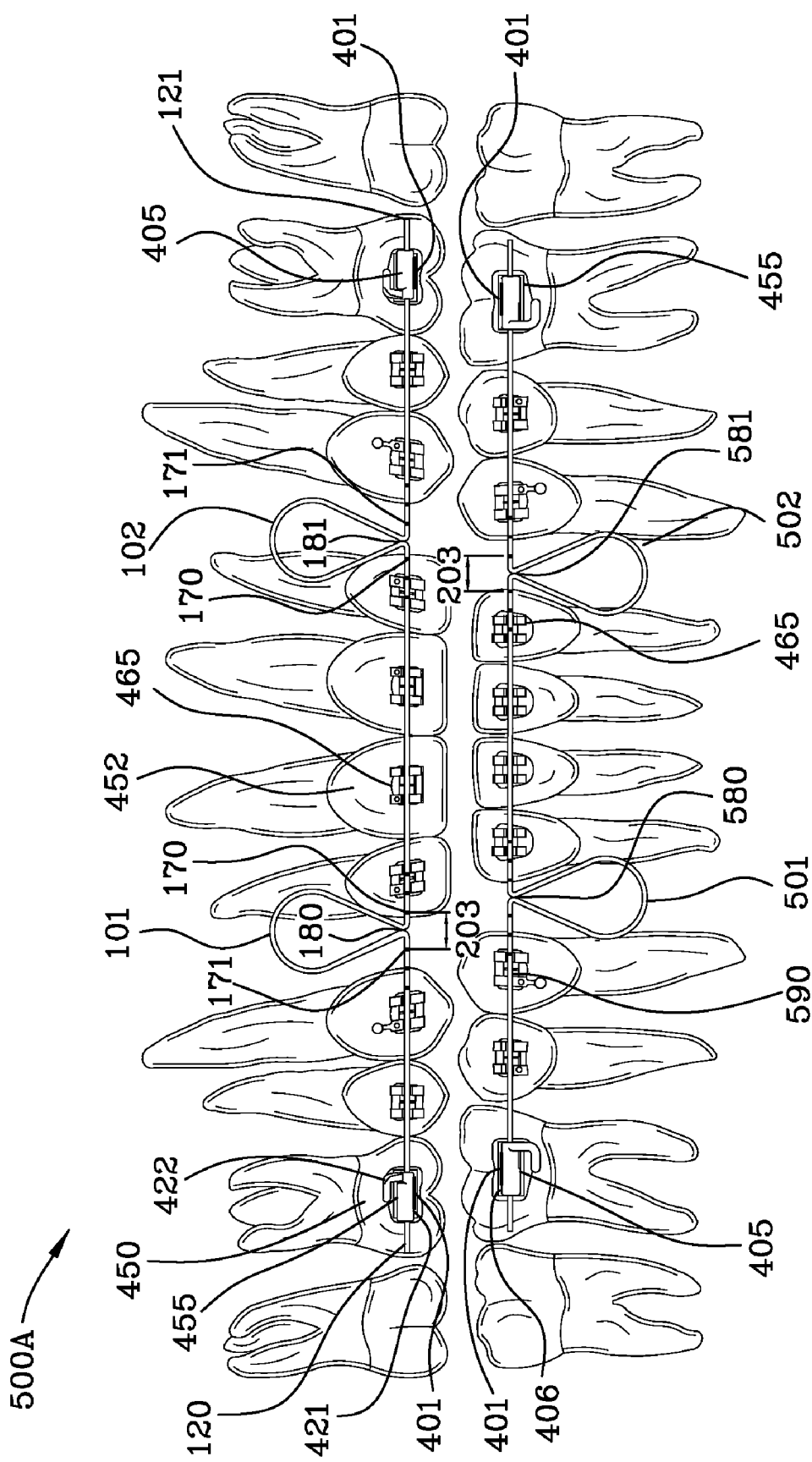
FIG. 5A is an orthographic projection of the orthodontic device applied to a patient's teeth with no load applied and the loop-springs deactivated.

FIG. 4F is a view 400F of an orthodontic molar bracket 455 including the pawl with an extendable archwire therethrough from the occlusal (chewing side) of the teeth when reference is made to FIGS. 5 and 5A. Arm 422 is illustrated in FIG. 4F and is used to connect other orthodontic structures thereto. Base 454 is affixed to the tooth of a patient or to an orthodontic band and a flange or transitional portion 420 interconnects the base with the molar bracket. The occlusal side 162 of the archwire 190 is viewed in FIG. 4F along with notches 105.

FIG. 4G is a view 400G of orthodontic molar bracket 405 with the pawl 403 removed therefrom illustrating the aperture 410 for receiving the pawl 403. Aperture 410 is illustrated as being rectangular but it is envisioned that it could be in any cross-sectional shape and that the cross-sectional shape could vary. As shown in FIG. 4G, aperture 410 communicates with passageway 408 and is arranged orthogonally with respect thereto. Alternate orientations of the pawl and the aperture are specifically contemplated. In other words, the pawl and the aperture may be oriented on the buccal side or the gingival side. FIG. 4H is a side view 400H of the orthodontic molar bracket 405 illustrating the passageway 408 therethrough and the arm 422.

FIG. 4I is an exploded assembly view 400G illustrating a molar bracket 405, pawl 403 and extendable archwire 190.

FIG. 4J is a view 400J illustrating a pawl 404A having a curved cam surface 404A. FIG. 4K is a partial cross-sectional view 400K of an orthodontic molar bracket 405 illustrating an aperture 410 in the occlusal portion, a pawl 403 affixed to the bracket using an elastomeric or metal ligature 485, and an extendable archwire having protrusions 106, 106A thereon inserted through the bracket. Slots or passageways 401B enable the ligation device to be inserted through the slot such that the ligation device resides partially under the pawl. Pawl 403 is able to pivot and to follow the contour of the archwire as it is alternately raised and lowered as the archwire is moved (extended) leftwardly when viewing FIGS. 4K and 4L.

FIG. 4L is partial cross-sectional view 400L of an orthodontic molar bracket similar to FIG. 4 with the stop surface 403A of the pawl 403 engaging the locking surface 106 of a protrusion. In FIG. 4L, the elastomeric device secures the pawl against the locking surface of the archwire.

FIG. 4M is a view 400M of an orthodontic molar bracket 455 similar to FIG. 4F including the pawl having slots 401B therein secured to the bracket 455 by an elastomeric or metal ligature device 485. Slot 401B terminates in port 401C having a diameter which is sufficiently larger than the elastomeric or metal ligature devices 485. The elastomeric or metal ligature device 485 is pressed into and through the slot 401B.

FIG. 5 is an orthographic projection 500 of the orthodontic device applied to the teeth 450, 452 of a patient with load applied and the loop-springs activated with a distance 203A therebetween. The orthodontic device includes the archwire and brackets as described in this specification. Intermediate brackets 465 guide the archwire and provide support thereto. Molar brackets 455 and 405 are illustrated in FIG. 5 along with archwires for the upper and lower teeth of the patient.

Use of the device includes anchoring one end of the archwire in the first instance. The anchor may be a molar or other bracket or another dental appliance such as a band or a wire. The adjustment end of the archwire is inserted into the passageway in the molar bracket. As the archwire is inserted into the passageway it overcomes the pawl lifting the pawl as necessary. Pawl 403 extends into the passageway or lumen 408 as viewed in FIGS. 4A and 4C.

Alternatively, if sheath 407 is used over the pawl extension 402, then pawl 403 is prohibited from entering the passageway 408 thus making insertion and retraction of the archwire easier. If pawl sheath 407 is used it will provide a seamless transition for orthodontists familiar with the prior art method of inserting the archwire into and through the passageway of the molar bracket.

The molar bracket used for adjustment of the archwire is, of course, first secured to a molar. There may be one or more intermediate guide devices such as brackets 465, 590 which guide and secure (anchor) the archwire and maintain its stability. For instance, the anchor may be in the form of a ligation to a bracket or brackets affixed to a tooth or teeth such as those shown in FIGS. 5 and 5A. These brackets may self-ligating brackets or the ligature may be affixed by the orthodontist. Further, another example of an anchor may be a molar bracket located on the other end of the archwire where it may engage a bracket such as that disclosed by the instant invention or a conventional bracket.

Once the archwire is inserted into a lumen or passageway of the molar bracket 405, 455, the orthodontist must ensure that the sheath 407 (if used) is removed if so desired to activate the loop. Then, the orthodontist forcefully pushes or pulls the archwire further through the molar bracket and while this is happening the pawl 403 rides along (i.e., follows) the contour of the occlusal side 162 of the adjustment portion 120A. The contour of the occlusal side 162 is either notched 105 or has protrusions 106, 106A as described above. As the orthodontist pushes or pulls the archwire further through the molar bracket, tension in the archwire increases as the spring loop is activated (deflected or opened). As the spring is activated (deflected), indicia (markings, engravings, embedded materials) spaced on the archwire located on either side of the spring move. In some instances such as those depicted, for example, in FIGS. 1-1C the indicia will move further apart upon activation of the open-loop spring 101, 102. In FIGS. 1D-1H, the indicia will move closer together upon activation of the closed-loop spring 101D, 102D. Distance measurements are then made by the orthodontist. Rulers, compasses, optical measuring devices or other devices (used to detect reference points either in the visible spectrum or not determine the distance between the marks.) Optical measuring devices may employ multiple indicia in determining the deflection distance (i.e., the distance between reference indicia).

Once the distance between the markings on the archwire is measured, the treating orthodontist is able to correlate the force (tension) applied to the teeth using the load curves (which plot force versus distance between the marks, i.e., activation opening of the spring) or an equation relating force to the distance between the markings for the specific archwire and spring being used. Force is defined as mass times acceleration. Force is expressed in Newtons (symbol N) which is equivalent to $kg\text{-}m/s^2$. Newtons divided by 0.0098066 equals grams-force. Typically, orthodontists express force as grams-force or Newtons.

FIG. 5A is an orthographic view 500A of the orthodontic device applied to the teeth 450, 452 of a patient with no load applied and the loop-springs deactivated. In FIG. 5A the archwire is secured to brackets 405, 455. The indicia (markings) on the archwire indicate that the loops are in their unloaded state. The archwire will be ligated or otherwise secured to brackets 465. Reference numerals 180, 181, 580, 581 represent the contact points between the respective open-loop springs.

The condition illustrated in FIG. 5 may be observed during initial application and treatment of the patient. It should be noted that during the treatment of a patient the orthodontist will review progress of the orthodontic device by periodically measuring the change in distance between the indicia or the rate of change of the distance between the indicia.

Readjustment of the tension during treatment of a patient may be necessary to increase or reduce the tension in the archwire. If tension is reduced the orthodontist will disengage the pawl extension arm 402 and urge the archwire in the anterior direction. Alternatively, the orthodontist may place the sheath over the pawl extension arm 402.

Figure 5B:
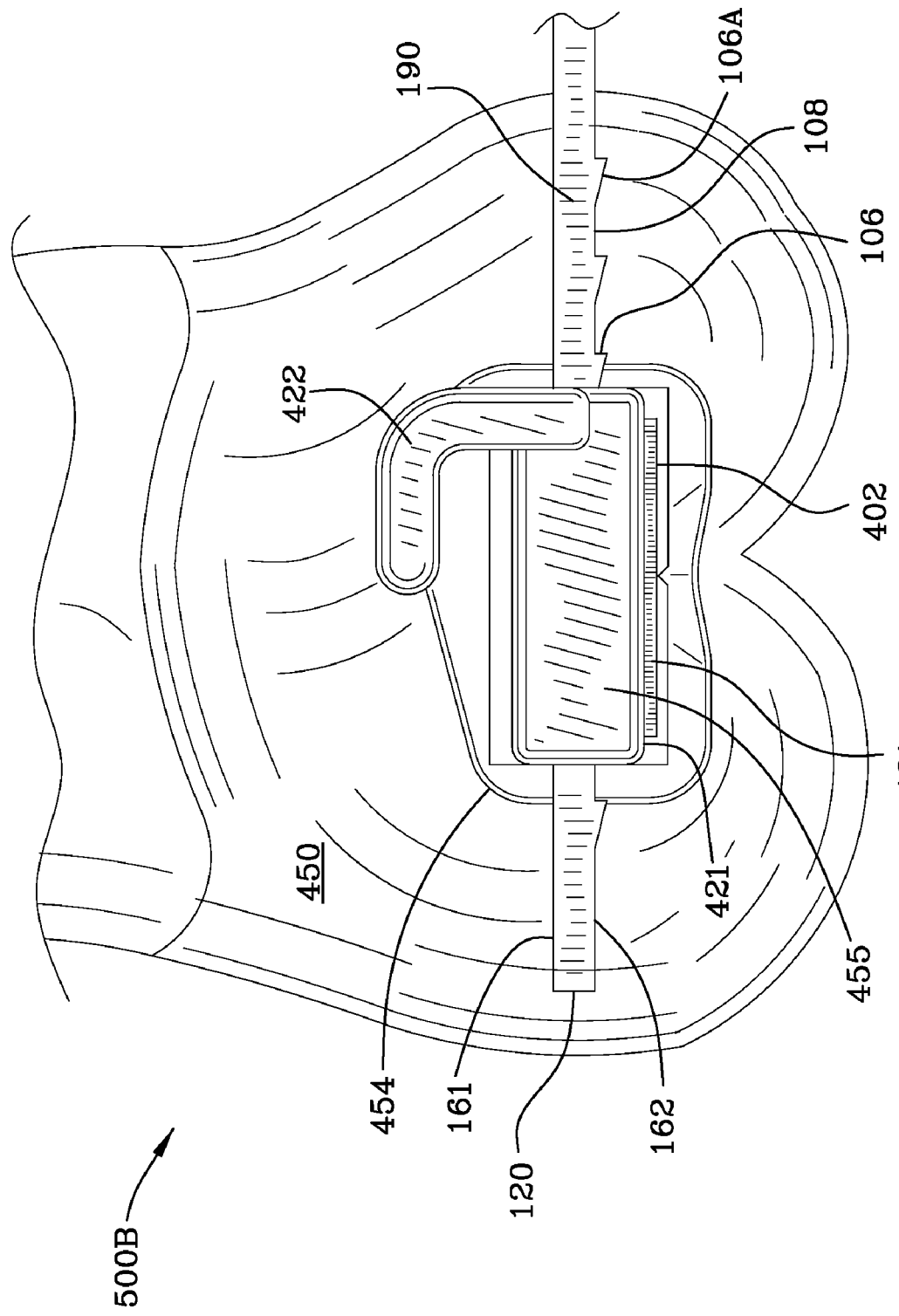
FIG. 5B is an enlargement of a bracket applied to a tooth.

FIG. 5B is an enlargement 500B of a molar bracket 455 applied to a tooth. Reference is made to FIG. 5 to identify and bracket 455. Pawl arm 401 and extension arm 402 are illustrated in FIG. 5B as located on the occlusal (grinding) side of the teeth as this gives the orthodontist greater access to the extension arm. If the example of FIG. 4D or 4E are used then access to the pawl extension arm is increased and these examples may facilitate initial treatment or readjustment of the archwire. FIG. 5C is an enlargement 500C of a bracket 455 applied to a tooth with the sheath 407 over a portion of the pawl extension arm 402. As illustrated in FIGS. 5C and 4E, the pawl does not engage the adjustment portion of the archwire.

Figure 6:
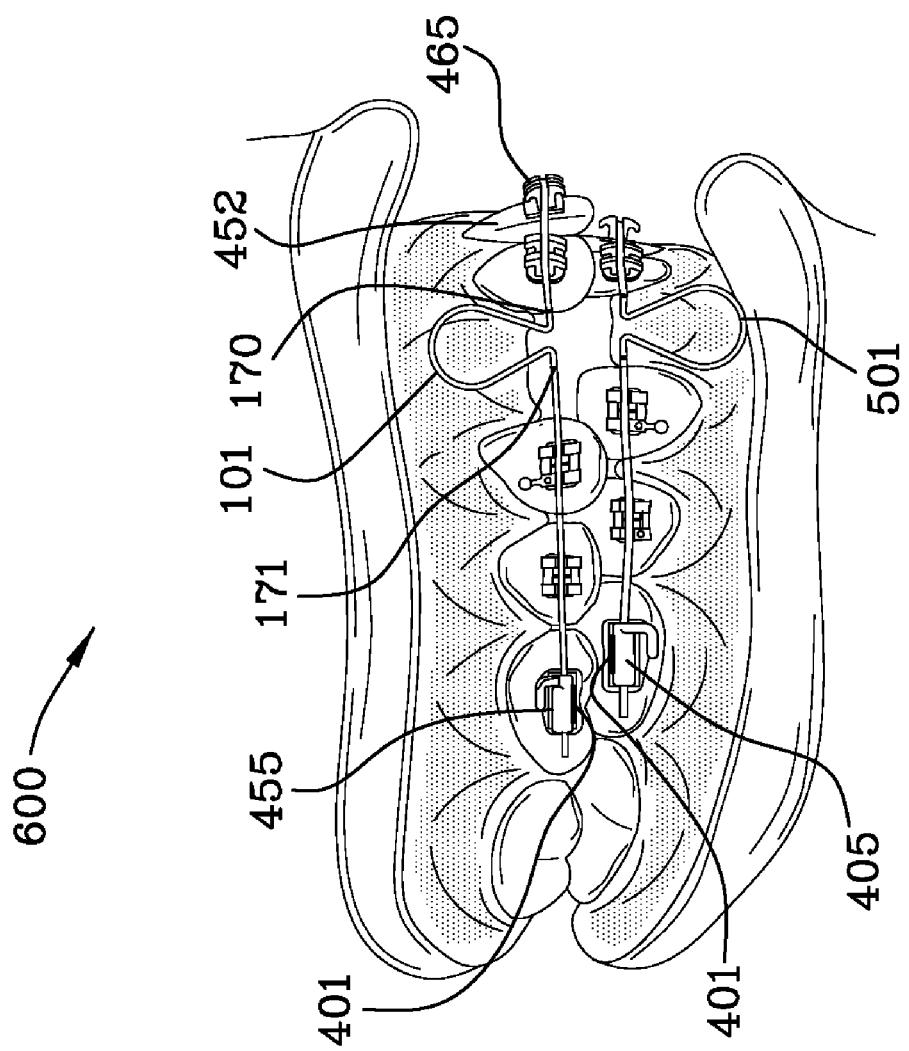
FIG. 6 is a perspective view of the orthodontic device applied to teeth with load applied and the loops-springs activated.

FIG. 6 is a perspective view 600 of the orthodontic device applied to teeth with load applied and the loops-springs 101, 102, 501, 502 activated.

Figure 7:
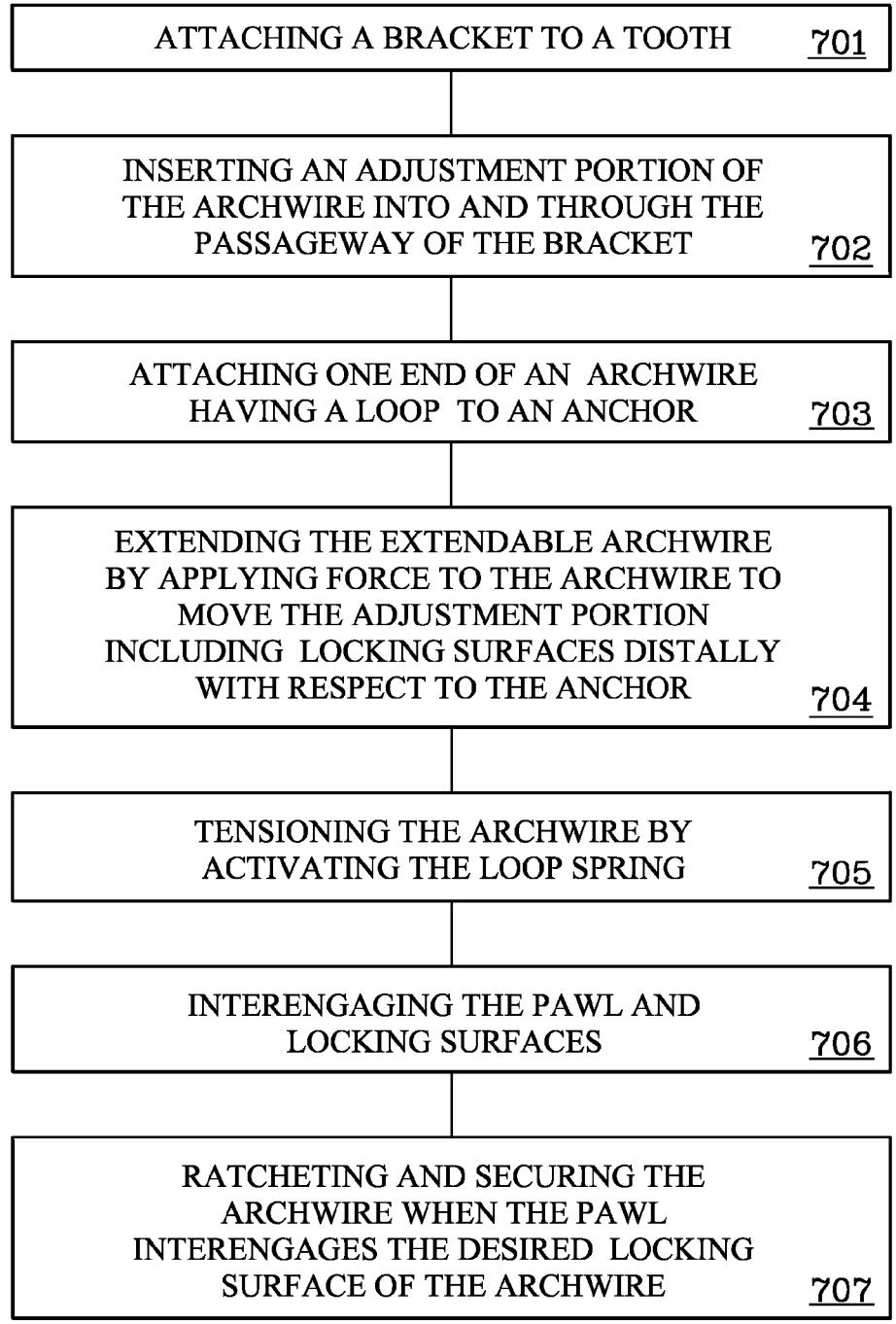
FIG. 7 is a block diagram of a treatment process.

FIG. 7 is a block diagram 700 of an example of a process for the treatment of a patient comprising the steps of attaching a bracket to a tooth 701, inserting an adjustment portion of the archwire into and through the passageway of the bracket 702, attaching one end of an archwire having a loop to an anchor 703, extending the extendable archwire by applying force to the archwire to move the adjustment portion including locking surfaces distally with respect to the anchor 704, tensioning the archwire by activating the loop spring 705, interengaging the pawl and locking surfaces 706, and ratcheting and securing the archwire when the pawl interengages the desired locking surface of the archwire 707.

A list of reference numerals to aid the reader follows.

REFERENCE NUMERALS

100 . . . perspective view of archwire with open-loop springs, notches, and marks
100A—perspective view of archwire with open-loop springs, notches in the adjustment portion and marks
100B—perspective view of archwire with open-loop springs, protrusions on the adjustment portion and marks
100C—perspective view of archwire with open-loop springs, protrusions on the adjustment portion and marks
100D—perspective view of archwire with closed-loop springs, notches in the adjustment portion and marks
100E—perspective view of archwire with closed-loop springs, notches in the adjustment portion and marks
100F—view of closed loop
100G—perspective view of archwire with closed-loop springs, protrusions in the adjustment portion and marks
100H—perspective view of archwire with closed-loop springs, protrusions in the adjustment portion and marks
101—first open-loop spring
101D—first closed-loop spring
102—second open-loop spring
102D—second closed-loop spring
103—labial (near lips)/buccal (near cheeks) side of archwire
104—lingual (near tongue) side of archwire
105—notch
105A—ramp of notch
105B—stop face of notch
106—stop face of protrusion
106A—ramp on protrusion
107—land portion of archwire between notches
107A—land portion of archwire between notches
108—land portion of archwire between protrusions
108A—land portion of archwire between protrusions
111—first leg (posterior leg) of first loop spring
111D, 112D, 114D, 115D—leg of closed loop spring
112—second leg (anterior leg) of first loop spring
113—intermediate portion of first open-loop spring
113D—intermediate portion of first closed-loop spring
114—second leg (anterior leg) of second open-loop spring
115—first leg (posterior leg) of second open-loop spring
116—intermediate portion of second open-loop spring
116D—intermediate portion of second closed-loop spring
120—first end of archwire
120A, 121A—adjustment portion of archwire
121—second end of archwire
131—first bend of first leg of first loop spring
131A, 132A—bend of first closed-loop spring
132—second bend of second leg of first loop spring
133A, 134A—bend of second-closed-loop spring
134—third bend of second leg of second loop spring
135—fourth bend of second leg of second loop spring
141, 142—gap between legs of closed loop spring
161—gum (gingival) side of archwire
162—occlusal (grinding side of teeth) side of archwire
170, 170A, 170B, 171, 171A, 171B, 178, 179, 201, 202—marks/indicia on archwire
180—unloaded gap between legs of first loop
181—unloaded gap between legs of second loop
190—archwire
200—view of a portion of the archwire, open-loop and notches with no load applied to archwire
200A—view of a portion of the archwire, open-loop and notches with a load applied to the archwire
200B—perspective view of a portion of the archwire, open-loop and notches with a load applied to the archwire
200C—perspective view of a portion of the archwire, open-loop and notches with a load applied to the archwire
200D, 200E, 200F, 200G—perspective view of exemplary loop
200H—enlarged portion of archwire and notch
200I—enlarged portion of archwire and protrusion
200J—illustration of protrusions closer together
200K—enlarged portion of archwire and notch
200L—illustration of notches closer together
203—distance between marks with no load on the archwire
203A—distance between marks with load applied to the archwire
203D, 203E, 203F, 203G—distance between marks
204—distance between stop faces of notches
205—width of notch
206—depth of notch
207—thickness of archwire in one direction
210—archwire drawing break
214D, 214E, 214F, 214G, 215D, 215E, 215F, 215G,—loop-legs
216D, 216E, 216F, 216G—intermediate portion of loops
217F, 218F, 219F—loops
300—view of an exemplary archwire with notches in the adjustment portion and no load applied to the archwire
300A—view of an exemplary archwire with load applied to the archwire
300B—perspective view of an exemplary archwire with load applied to the archwire
300C—perspective view of an exemplary archwire with protrusions in the adjustment portion and a load applied to the archwire
301—loop at end of archwire
321—end of loop
400—cross-sectional view of orthodontic molar bracket, pawl and archwire with protrusions on the adjustment portion in an unlocked position
400A—cross-sectional view of orthodontic molar bracket, pawl and archwire with protrusions on the adjustment portion in locked position
400B—cross-sectional view of orthodontic molar bracket, pawl and archwire with notches in the adjustment portion in an unlocked position
400C—cross-sectional view of orthodontic molar bracket, pawl and archwire with notches in the adjustment portion in locked position;
400D—cross-sectional view of orthodontic molar bracket, pawl and archwire with protrusion on the adjustment portion in locked position
400E—cross-sectional view of orthodontic molar bracket, pawl, pawl sheath and archwire with notches in the adjustment portion in unlocked position
400F—bottom view of orthodontic molar bracket 455

400G—top view of orthodontic molar bracket 405 with pawl removed
400H—distal end view of orthodontic molar bracket 405
400I—exploded front view of orthodontic molar bracket 405, pawl, and adjustment portion of archwire
400J—pawl with curved cam surface
400K—cross-section of bracket with elastomeric securement of pawl
400L—cross-section of bracket with elastomeric securement of pawl to prevent retraction of archwire
400M—example of elastomeric device securing pawl to bracket
401—pawl arm
401A—attachment of pawl arm
401B—slot in pawl for receiving elastomeric device
401C—port in pawl
402—extension arm of pawl
403—pawl
403A—stop surface of pawl
404—pawl cam surface
404A—pawl curved cam surface
405—orthodontic molar bracket
405A, 406—body portion of orthodontic molar bracket
407—sheath
408—passageway of pawl
409—end of upper body portion 406
410—aperture in body of orthodontic molar bracket
420—flange of molar bracket
421—upper surface of molar orthodontic bracket 405
422—arm of orthodontic molar bracket
430—studs on pawl extension arm to hold sheath
450—molar
452—tooth
454—base
455—orthodontic molar bracket
465—intermediate bracket
470—notch in pawl
471—notch in body for opening
485—elastomeric or metal ligature device
500—orthographic view of an archwire and orthodontic molar brackets and teeth illustrating the interrelationship thereof with load applied to the archwire
500A—orthographic view of an archwire and orthodontic molar brackets and teeth illustrating the interrelationship thereof with no load applied to the archwire
500B—enlarged front view of orthodontic molar bracket 455
500C—enlarged front view of orthodontic molar bracket with sheath over pawl extension
501, 502—loop spring
580, 581—gap, no load
590—top side of archwire
600—perspective view of archwires and brackets applied to teeth of patient
600A—side view of archwire and brackets applied to teeth of patient
700—block diagram of process
701—attaching a bracket to a tooth
702—inserting an adjustment portion of the archwire into and through the passageway of the bracket
703—attaching one end of an archwire having a loop to an anchor
704—extending the extendable archwire by applying force to the archwire by applying force to the archwire to move the adjustment portion including locking surfaces distally with respect to the anchor
705—tensioning the archwire by activating the loop spring
706—interengaging the pawl and locking surfaces ratcheting and securing the archwire when the pawl interengages the desired locking surface of the archwire Those skilled in the art will recognize that changes may be made to the invention which has been set forth above by way of example without departing from the spirit and the scope of the invention as defined by the claims as set forth below.

We claim:

1. An orthodontic bracket, comprising: a base; a body, said body includes external surfaces; said body and said base being one-piece; an archwire passageway, said archwire passageway extending through said body; an aperture extending from one of said external surfaces of said body to said archwire passageway; a pawl attached to said bracket and which extends into said aperture extending from one of said external surfaces of said body to said archwire passageway of said bracket; and, said pawl includes an extension arm and wherein a sheath removably resides over said extension arm.

2. An orthodontic bracket according to claim 1 wherein said pawl includes a cam surface and a stop surface.

3. An orthodontic device, comprising:
a bracket; said bracket includes a body and said body includes external surfaces; an archwire passageway formed in said body; an aperture extending from one of said external surfaces of said body to said passageway; a pawl attached to said body, said pawl includes stop and cam surfaces; and, said pawl extends into said aperture of said bracket;
an extendable archwire; said extendable archwire includes an adjustment portion having a locking surface and a loop spring therein; said adjustment portion of said extendable archwire being inserted into and through said passageway of said bracket residing partially in said passageway of said bracket; said adjustment portion of said extendable archwire is movable with respect to and within said passageway of said bracket;
said loop spring in said extendable archwire resisting extension of said extendable archwire upon the application of force to said extendable archwire activating said loop spring; said loop spring in said extendable archwire retracting said extendable archwire upon the discontinuation of the application of force to said extendable archwire;
said pawl of said bracket and said locking surface of said adjustment portion of said extendable archwire form a ratchet; said cam surface of said pawl interengages said extendable archwire as said extendable archwire is extended through said bracket under the application of force to said extendable archwire; and, said stop surface of said pawl interengages said locking surface of said adjustment portion of said extendable archwire preventing retraction of said extendable archwire upon discontinuation of the application of force.

4. An orthodontic device as claimed in claim 3 wherein said adjustment portion of said extendable archwire includes a notch therein and wherein said locking surface is formed in said notch.

5. An orthodontic device as claimed in claim 4 wherein said adjustment portion of said extendable archwire includes a plurality of notches therein and wherein each of said notches includes a locking surface enabling selection and adjustment of the extension of said extendable archwire.

6. An orthodontic device according to claim 4 wherein: said loop spring has first and second sides, said loop spring interposed in said archwire, said archwire extending from said first and second sides of said loop spring; and, indicia residing in or on said archwire, said indicia residing on said first and second sides of said loop spring and in proximity to said loop spring.

7. An orthodontic device as claimed in claim 3 wherein said adjustment portion of said extendable archwire includes a protrusion thereon and wherein said locking surface is formed on said protrusion.

8. An orthodontic device as claimed in claim 7 wherein said adjustment portion of said extendable archwire includes a plurality of protrusions thereon and wherein each of said protrusions includes a locking surface enabling selection and adjustment of the extension of said extendable archwire.

9. An orthodontic device as claimed in claim 3 further comprising indicia in proximity to said loop spring.

10. An orthodontic device according to claim 3 wherein: said loop spring has first and second sides, said loop spring interposed in said archwire, said archwire extending from said first and second sides of said loop spring; and, indicia residing in or on said archwire, said indicia residing on said first and second sides of said loop spring and in proximity to said loop spring.

* * * * *